(12) United States Patent
Casiello et al.

(10) Patent No.: US 10,166,321 B2
(45) Date of Patent: Jan. 1, 2019

(54) HIGH-FLOW PORT AND INFUSION NEEDLE SYSTEMS

(71) Applicants: Damon Casiello, Lowell, MA (US); Kenneth LeBlanc, Chelmsford, MA (US); Marissa Kewley, Medford, MA (US); Mark Girard, Medway, MA (US)

(72) Inventors: Damon Casiello, Lowell, MA (US); Kenneth LeBlanc, Chelmsford, MA (US); Marissa Kewley, Medford, MA (US); Mark Girard, Medway, MA (US)

(73) Assignee: AngioDynamics, Inc., Latham, NY (US)

( * ) Notice: Subject to any disclaimer, the term of this patent is extended or adjusted under 35 U.S.C. 154(b) by 735 days.

(21) Appl. No.: 14/593,502

(22) Filed: Jan. 9, 2015

(65) Prior Publication Data
US 2016/0199560 A1  Jul. 14, 2016

(51) Int. Cl.
A61M 1/36 (2006.01)
A61M 39/02 (2006.01)
A61M 5/32 (2006.01)
A61M 39/00 (2006.01)

(52) U.S. Cl.
CPC ........ A61M 1/3659 (2014.02); A61M 1/3653 (2013.01); A61M 5/3286 (2013.01); A61M 39/0208 (2013.01); A61M 2039/0054 (2013.01); A61M 2039/0211 (2013.01)

(58) Field of Classification Search
CPC ............ A61M 1/3659; A61M 39/0208; A61M 1/3496; A61M 1/3653; A61M 2039/0054; A61M 2039/0211; A61M 39/04; A61M 5/3286
See application file for complete search history.

(56) References Cited

U.S. PATENT DOCUMENTS

| | | | |
|---|---|---|---|
| 1,653,819 A | 12/1927 | Northcott et al. | |
| 3,094,124 A | 6/1963 | Birtwell | |
| 3,392,183 A | 7/1968 | Windemuth | |
| 3,427,366 A | 2/1969 | Verdol et al. | |
| 3,438,375 A | 4/1969 | Ericson | |

(Continued)

FOREIGN PATENT DOCUMENTS

| | | |
|---|---|---|
| DE | 4000893 A1 | 7/1991 |
| EP | 0378132 A2 | 7/1990 |

(Continued)

OTHER PUBLICATIONS

Guiffant, et al, Impact of the Shape of the Implantable Ports on their Efficiency of flow (Injection and Flushing), Medical Devices: Evidence and Research 2014:7, pp. 319-324.

(Continued)

Primary Examiner — Brandy S Lee
(74) Attorney, Agent, or Firm — Zachary F Madonna

(57) ABSTRACT

The present invention relates to a multi-reservoir port, catheter and non-coring needle systems that support high-flow applications such as hemodialysis and apheresis. In particular, the present invention relates to improvements to each of these systems to provide optimal flow rates and septum life with minimal intraluminal pressure; both individually and in combination.

14 Claims, 8 Drawing Sheets

(56) References Cited

U.S. PATENT DOCUMENTS

| | | |
|---|---|---|
| 3,872,058 A | 3/1975 | Gresham |
| 3,971,376 A | 7/1976 | Wichterle |
| 3,978,157 A | 8/1976 | Bottenbruch et al. |
| 4,016,886 A | 4/1977 | Doss et al. |
| 4,054,139 A | 10/1977 | Crossley |
| 4,142,525 A | 3/1979 | Binard et al. |
| 4,226,246 A | 10/1980 | Fragnet |
| 4,245,635 A | 1/1981 | Kontos |
| 4,248,224 A | 2/1981 | Jones |
| 4,262,672 A | 4/1981 | Kief |
| 4,309,994 A | 1/1982 | Grunwald |
| 4,312,907 A | 1/1982 | Hiraoka et al. |
| 4,403,983 A | 9/1983 | Edelman et al. |
| 4,405,305 A | 9/1983 | Stephen et al. |
| 4,407,943 A | 10/1983 | Cole et al. |
| 4,423,740 A | 1/1984 | Castle et al. |
| 4,425,119 A | 1/1984 | Berglund |
| 4,468,224 A | 8/1984 | Enzmann et al. |
| 4,469,483 A | 9/1984 | Becker et al. |
| 4,483,688 A | 11/1984 | Akiyama |
| 4,543,088 A | 9/1985 | Bootman et al. |
| 4,563,180 A | 1/1986 | Jervis et al. |
| 4,569,673 A | 2/1986 | Tesi |
| 4,571,749 A | 2/1986 | Fischell |
| 4,584,362 A | 4/1986 | Leckart et al. |
| 4,587,954 A | 5/1986 | Haber |
| 4,592,920 A | 6/1986 | Murtfeldt |
| 4,603,152 A | 7/1986 | Laurin et al. |
| 4,623,327 A | 11/1986 | Mahurkar |
| 4,645,495 A | 2/1987 | Vaillancourt |
| 4,661,530 A | 4/1987 | Gogolewski et al. |
| 4,673,394 A | 6/1987 | Fenton, Jr. et al. |
| 4,692,146 A | 9/1987 | Hilger |
| 4,710,174 A | 12/1987 | Moden et al. |
| 4,742,090 A | 5/1988 | Hunter et al. |
| 4,767,410 A | 8/1988 | Moden et al. |
| 4,769,005 A | 9/1988 | Ginsburg et al. |
| 4,778,452 A | 10/1988 | Moden et al. |
| 4,781,680 A | 11/1988 | Redmond et al. |
| 4,781,695 A | 11/1988 | Dalton |
| 4,788,083 A | 11/1988 | Dammann et al. |
| 4,792,354 A | 12/1988 | Matsuo et al. |
| 4,804,359 A | 2/1989 | Grunwald et al. |
| 4,808,156 A | 2/1989 | Dean |
| 4,810,963 A | 3/1989 | Blake-Coleman et al. |
| 4,822,341 A | 4/1989 | Colone |
| 4,838,269 A | 6/1989 | Robinson et al. |
| 4,838,873 A | 6/1989 | Landskron et al. |
| 4,857,053 A | 8/1989 | Dalton |
| 4,861,830 A | 8/1989 | Ward, Jr. |
| 4,886,501 A | 12/1989 | Johnston et al. |
| 4,886,502 A | 12/1989 | Poirier et al. |
| 4,892,518 A | 1/1990 | Cupp et al. |
| 4,897,081 A | 1/1990 | Poirier et al. |
| 4,902,503 A | 2/1990 | Umemura et al. |
| 4,907,601 A | 3/1990 | Frick |
| 4,929,236 A | 5/1990 | Sampson |
| 4,944,726 A | 7/1990 | Hilal et al. |
| 4,946,793 A | 8/1990 | Marshall, III |
| 4,954,130 A | 9/1990 | Edwards |
| 4,955,861 A | 9/1990 | Enegren et al. |
| 4,966,586 A | 10/1990 | Vaillancourt |
| 4,983,162 A | 1/1991 | Metais et al. |
| 4,994,503 A | 2/1991 | Harris et al. |
| 4,999,210 A | 3/1991 | Solomon et al. |
| 5,013,304 A | 5/1991 | Russell et al. |
| 5,019,034 A | 5/1991 | Weaver et al. |
| 5,019,096 A | 5/1991 | Fox, Jr. et al. |
| 5,041,098 A | 8/1991 | Loiterman et al. |
| 5,052,391 A | 10/1991 | Silberstone et al. |
| 5,053,013 A | 10/1991 | Ensminger et al. |
| 5,053,023 A | 10/1991 | Martin |
| 5,053,423 A | 10/1991 | Liu |
| 5,058,605 A | 10/1991 | Slovak |
| 5,059,170 A | 10/1991 | Cameron |
| 5,064,871 A | 11/1991 | Sciangola |
| 5,069,206 A | 12/1991 | Crosbie |
| 5,084,015 A | 1/1992 | Moriuchi |
| 5,092,849 A | 3/1992 | Sampson |
| 5,098,843 A | 3/1992 | Calvin |
| 5,125,893 A | 6/1992 | Dryden |
| 5,129,887 A | 7/1992 | Euteneuer et al. |
| 5,129,891 A | 7/1992 | Young |
| 5,133,742 A | 7/1992 | Pinchuk |
| 5,134,070 A | 7/1992 | Casnig |
| 5,137,529 A | 8/1992 | Watson et al. |
| 5,145,727 A | 9/1992 | Potts et al. |
| 5,149,576 A | 9/1992 | Potts et al. |
| 5,151,231 A | 9/1992 | Lambert et al. |
| 5,167,638 A | 12/1992 | Felix et al. |
| 5,171,305 A | 12/1992 | Schickling et al. |
| 5,173,158 A | 12/1992 | Schmukler |
| 5,178,612 A | 1/1993 | Fenton, Jr. |
| 5,180,365 A | 1/1993 | Ensminger et al. |
| 5,193,537 A | 3/1993 | Freeman |
| 5,203,771 A | 4/1993 | Melker et al. |
| 5,205,834 A | 4/1993 | Moorehead et al. |
| 5,213,574 A | 5/1993 | Tucker |
| D337,637 S | 7/1993 | Tucker |
| 5,229,431 A | 7/1993 | Pinchuk |
| 5,236,417 A | 8/1993 | Wallis |
| 5,240,675 A | 8/1993 | Wilk et al. |
| 5,242,415 A | 9/1993 | Kantrowitz et al. |
| 5,242,995 A | 9/1993 | Kim et al. |
| 5,249,598 A | 10/1993 | Schmidt |
| 5,250,038 A | 10/1993 | Melker et al. |
| 5,260,020 A | 11/1993 | Wilk et al. |
| 5,263,930 A | 11/1993 | Ensminger |
| 5,273,525 A | 12/1993 | Hofmann |
| 5,281,199 A | 1/1994 | Ensminger et al. |
| 5,281,205 A | 1/1994 | McPherson |
| 5,283,194 A | 2/1994 | Schmukler |
| 5,300,048 A | 4/1994 | Drewes, Jr. et al. |
| 5,312,337 A | 5/1994 | Flaherty et al. |
| 5,318,545 A | 6/1994 | Tucker |
| 5,318,563 A | 6/1994 | Malis et al. |
| 5,328,451 A | 7/1994 | Davis et al. |
| 5,330,449 A | 7/1994 | Prichard et al. |
| 5,334,171 A | 8/1994 | Kaldany |
| 5,350,360 A | 9/1994 | Ensminger et al. |
| 5,352,204 A | 10/1994 | Ensminger |
| 5,356,381 A | 10/1994 | Ensminger et al. |
| 5,370,624 A | 12/1994 | Edwards et al. |
| 5,372,582 A | 12/1994 | Skrabal et al. |
| 5,373,855 A | 12/1994 | Skrabal et al. |
| 5,387,192 A | 2/1995 | Glantz et al. |
| 5,389,069 A | 2/1995 | Weaver |
| 5,395,525 A | 3/1995 | Takano et al. |
| 5,399,168 A | 3/1995 | Wadsworth, Jr. et al. |
| 5,403,291 A | 4/1995 | Abrahamson |
| 5,403,311 A | 4/1995 | Abele et al. |
| 5,405,340 A | 4/1995 | Fageol et al. |
| 5,417,656 A | 5/1995 | Ensminger et al. |
| 5,421,814 A | 6/1995 | Geary |
| 5,423,334 A | 6/1995 | Jordan |
| 5,425,752 A | 6/1995 | Vu'Nguyen |
| 5,439,440 A | 8/1995 | Hofmann |
| 5,445,608 A | 8/1995 | Chen et al. |
| 5,458,582 A | 10/1995 | Nakao |
| 5,458,625 A | 10/1995 | Kendall |
| 5,476,451 A | 12/1995 | Ensminger et al. |
| 5,486,570 A | 1/1996 | St. Clair |
| 5,509,897 A | 4/1996 | Twardowski et al. |
| 5,514,127 A | 5/1996 | Shanks |
| 5,520,632 A | 5/1996 | Leveen et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,527,307 A | 6/1996 | Srisathapat et al. |
| 5,531,684 A | 7/1996 | Ensminger et al. |
| 5,533,999 A | 7/1996 | Hood et al. |
| 5,536,240 A | 7/1996 | Edwards et al. |
| 5,542,200 A | 8/1996 | Matsuoka |
| 5,542,923 A | 8/1996 | Ensminger et al. |

(56) References Cited

U.S. PATENT DOCUMENTS

| | | | |
|---|---|---|---|
| 5,542,937 | A | 8/1996 | Chee et al. |
| 5,543,200 | A | 8/1996 | Hargis et al. |
| 5,549,576 | A | 8/1996 | Patterson et al. |
| 5,554,117 | A | 9/1996 | Ensminger et al. |
| 5,556,381 | A | 9/1996 | Ensminger et al. |
| 5,558,641 | A | 9/1996 | Glantz et al. |
| 5,562,617 | A | 10/1996 | Finch, Jr. et al. |
| 5,562,618 | A | 10/1996 | Cai et al. |
| 5,569,182 | A | 10/1996 | Twardowski et al. |
| 5,571,152 | A | 11/1996 | Chen et al. |
| 5,575,769 | A | 11/1996 | Vaillancourt |
| 5,575,811 | A | 11/1996 | Reid et al. |
| 5,589,563 | A | 12/1996 | Ward et al. |
| 5,607,393 | A | 3/1997 | Ensminger et al. |
| 5,613,945 | A | 3/1997 | Cai et al. |
| 5,613,974 | A | 3/1997 | Andreas et al. |
| 5,614,136 | A | 3/1997 | Pepin et al. |
| 5,626,146 | A | 5/1997 | Barber et al. |
| 5,634,899 | A | 6/1997 | Shapland et al. |
| 5,637,877 | A | 6/1997 | Sinofsky |
| 5,643,197 | A | 7/1997 | Brucker et al. |
| 5,647,859 | A | 7/1997 | Lampropoulos et al. |
| RE35,601 | E | 9/1997 | Eckenhoff |
| 5,662,616 | A | 9/1997 | Bousquet |
| 5,662,913 | A | 9/1997 | Capelli |
| 5,674,267 | A | 10/1997 | Mir et al. |
| 5,676,656 | A | 10/1997 | Brimhall |
| 5,681,289 | A | 10/1997 | Wilcox et al. |
| 5,695,482 | A | 12/1997 | Kaldany |
| 5,695,490 | A | 12/1997 | Flaherty et al. |
| 5,702,359 | A | 12/1997 | Hofmann et al. |
| 5,702,363 | A | 12/1997 | Flaherty |
| 5,702,754 | A | 12/1997 | Zhong |
| 5,704,915 | A | 1/1998 | Melsky et al. |
| 5,713,844 | A | 2/1998 | Peyman |
| 5,720,921 | A | 2/1998 | Meserol |
| 5,723,718 | A | 3/1998 | Berens |
| 5,725,510 | A | 3/1998 | Hartmann et al. |
| 5,741,228 | A | 4/1998 | Lambrecht et al. |
| 5,776,096 | A | 7/1998 | Fields |
| 5,778,894 | A | 7/1998 | Dorogi et al. |
| 5,779,897 | A | 7/1998 | Kalthod et al. |
| 5,782,882 | A | 7/1998 | Lerman et al. |
| 5,792,104 | A | 8/1998 | Speckman et al. |
| 5,792,123 | A | 8/1998 | Ensminger |
| 5,795,326 | A | 8/1998 | Siman |
| 5,797,886 | A | 8/1998 | Roth et al. |
| 5,800,378 | A | 9/1998 | Edwards et al. |
| 5,800,414 | A | 9/1998 | Cazal |
| 5,810,762 | A | 9/1998 | Hofmann |
| 5,810,776 | A | 9/1998 | Bacich et al. |
| 5,810,789 | A | 9/1998 | Powers et al. |
| 5,817,072 | A | 10/1998 | Lampropoulos et al. |
| 5,830,172 | A | 11/1998 | Leveen et al. |
| 5,830,196 | A | 11/1998 | Hicks |
| 5,830,526 | A | 11/1998 | Wilson et al. |
| 5,833,654 | A | 11/1998 | Powers et al. |
| 5,836,905 | A | 11/1998 | Lemelson et al. |
| 5,836,935 | A | 11/1998 | Ashton et al. |
| 5,840,063 | A | 11/1998 | Flaherty |
| 5,843,026 | A | 12/1998 | Edwards et al. |
| 5,855,203 | A | 1/1999 | Matter |
| 5,873,849 | A | 2/1999 | Bernard |
| 5,876,366 | A | 3/1999 | Dykstra et al. |
| 5,879,322 | A | 3/1999 | Lattin et al. |
| 5,879,333 | A | 3/1999 | Smith |
| 5,879,499 | A | 3/1999 | Corvi |
| 5,882,341 | A | 3/1999 | Bousquet |
| 5,902,279 | A * | 5/1999 | Powles ............ A61B 10/0283 600/578 |
| 5,906,596 | A | 5/1999 | Tallarida |
| 5,908,701 | A | 6/1999 | Jennings et al. |
| 5,919,142 | A | 7/1999 | Boone et al. |
| 5,928,174 | A | 7/1999 | Gibbins |
| 5,929,201 | A | 7/1999 | Gibbons et al. |
| 5,944,688 | A | 8/1999 | Lois |
| 5,947,889 | A | 9/1999 | Hehrlein |
| 5,951,512 | A | 9/1999 | Dalton |
| 5,954,691 | A | 9/1999 | Prosl |
| 5,954,966 | A | 9/1999 | Matsuura et al. |
| 5,957,890 | A | 9/1999 | Mann et al. |
| 5,967,490 | A | 10/1999 | Pike |
| 5,983,131 | A | 11/1999 | Weaver et al. |
| 5,989,216 | A | 11/1999 | Johnson et al. |
| 5,991,697 | A | 11/1999 | Nelson et al. |
| 5,999,847 | A | 12/1999 | Elstrom |
| 6,001,079 | A | 12/1999 | Pourchez |
| 6,001,080 | A | 12/1999 | Kuracina et al. |
| 6,009,347 | A | 12/1999 | Hofmann |
| 6,010,613 | A | 1/2000 | Walters et al. |
| 6,016,452 | A | 1/2000 | Kasevich |
| 6,030,411 | A | 2/2000 | Lawandy |
| 6,033,393 | A | 3/2000 | Balbierz et al. |
| 6,039,712 | A * | 3/2000 | Fogarty ............ A61M 39/0208 604/175 |
| 6,041,252 | A | 3/2000 | Walker et al. |
| 6,055,453 | A | 4/2000 | Hofmann et al. |
| 6,068,650 | A | 5/2000 | Hofmann et al. |
| 6,085,115 | A | 7/2000 | Weaver et al. |
| 6,086,555 | A | 7/2000 | Eliasen et al. |
| 6,090,106 | A | 7/2000 | Goble et al. |
| 6,093,180 | A | 7/2000 | Elsberry |
| 6,099,508 | A | 8/2000 | Bousquet |
| 6,102,884 | A | 8/2000 | Squitieri |
| 6,102,885 | A | 8/2000 | Bass |
| 6,106,521 | A | 8/2000 | Blewett et al. |
| 6,109,270 | A | 8/2000 | Mah et al. |
| 6,111,049 | A | 8/2000 | Sendijarevic et al. |
| 6,120,492 | A | 9/2000 | Finch et al. |
| 6,122,599 | A | 9/2000 | Mehta |
| 6,127,485 | A | 10/2000 | Klun et al. |
| 6,127,507 | A | 10/2000 | Santerre |
| 6,132,416 | A | 10/2000 | Broselow |
| 6,132,419 | A | 10/2000 | Hofmann |
| 6,159,163 | A | 12/2000 | Strauss et al. |
| 6,177,522 | B1 | 1/2001 | Brady et al. |
| 6,197,845 | B1 | 3/2001 | Janssen et al. |
| 6,197,846 | B1 | 3/2001 | Combe et al. |
| 6,200,338 | B1 | 3/2001 | Solomon et al. |
| 6,208,893 | B1 | 3/2001 | Hofmann |
| 6,210,402 | B1 | 4/2001 | Olsen et al. |
| 6,212,433 | B1 | 4/2001 | Behl |
| 6,213,973 | B1 | 4/2001 | Eliasen et al. |
| 6,213,995 | B1 | 4/2001 | Steen et al. |
| 6,216,034 | B1 | 4/2001 | Hofmann et al. |
| 6,217,566 | B1 | 4/2001 | Ju et al. |
| 6,219,577 | B1 | 4/2001 | Brown, III et al. |
| 6,227,200 | B1 | 5/2001 | Crump et al. |
| 6,228,088 | B1 | 5/2001 | Miller et al. |
| 6,241,702 | B1 | 6/2001 | Lundquist et al. |
| 6,245,039 | B1 | 6/2001 | Brugger et al. |
| 6,254,645 | B1 | 7/2001 | Kellis, Jr. et al. |
| 6,261,831 | B1 | 7/2001 | Agee |
| 6,273,404 | B1 | 8/2001 | Holman et al. |
| 6,278,895 | B1 | 8/2001 | Bernard |
| 6,280,423 | B1 | 8/2001 | Davey et al. |
| 6,300,108 | B1 | 10/2001 | Rubinsky et al. |
| 6,326,177 | B1 | 12/2001 | Schoenbach et al. |
| 6,347,247 | B1 | 2/2002 | Dev et al. |
| 6,349,233 | B1 | 2/2002 | Adams |
| 6,351,674 | B2 | 2/2002 | Silverstone |
| 6,353,057 | B1 | 3/2002 | He et al. |
| 6,355,020 | B1 | 3/2002 | Bousquet |
| 6,355,858 | B1 | 3/2002 | Gibbins |
| 6,368,658 | B1 | 4/2002 | Schwarz et al. |
| 6,375,637 | B1 | 4/2002 | Campbell et al. |
| 6,387,105 | B1 | 5/2002 | Gifford, III et al. |
| 6,387,671 | B1 | 5/2002 | Rubinsky et al. |
| 6,403,348 | B1 | 6/2002 | Rubinsky et al. |
| 6,409,700 | B1 | 6/2002 | Siegel, Jr. et al. |
| 6,419,643 | B1 | 7/2002 | Shimada et al. |
| 6,419,674 | B1 | 7/2002 | Bowser et al. |
| 6,428,513 | B1 | 8/2002 | Abrahamson |
| 6,442,415 | B1 | 8/2002 | Bis et al. |

(56) References Cited

U.S. PATENT DOCUMENTS

| | | |
|---|---|---|
| 6,446,671 B2 | 9/2002 | Armenia et al. |
| 6,448,364 B1 | 9/2002 | Clatty et al. |
| 6,461,568 B1 | 10/2002 | Eckhardt |
| 6,461,569 B1 | 10/2002 | Boudreaux |
| 6,470,211 B1 | 10/2002 | Ideker et al. |
| 6,482,619 B1 | 11/2002 | Rubinsky et al. |
| 6,493,592 B1 | 12/2002 | Leonard et al. |
| 6,500,173 B2 | 12/2002 | Underwood et al. |
| 6,517,520 B2 | 2/2003 | Chang et al. |
| 6,526,320 B2 | 2/2003 | Mitchell |
| 6,530,951 B1 | 3/2003 | Bates et al. |
| 6,545,097 B2 | 4/2003 | Pinchuk et al. |
| 6,551,346 B2 | 4/2003 | Crossley |
| 6,562,604 B2 | 5/2003 | Rubinsky et al. |
| 6,575,959 B1 | 6/2003 | Sarge et al. |
| 6,592,544 B1 | 7/2003 | Mooney et al. |
| 6,595,966 B2 | 7/2003 | Davey et al. |
| 6,605,075 B1 | 8/2003 | Burdulis |
| 6,605,751 B1 | 8/2003 | Gibbins et al. |
| 6,607,529 B1 | 8/2003 | Jones et al. |
| 6,610,046 B1 | 8/2003 | Usami et al. |
| 6,611,706 B2 | 8/2003 | Avrahami et al. |
| 6,613,211 B1 | 9/2003 | McCormick et al. |
| 6,627,421 B1 | 9/2003 | Unger et al. |
| 6,629,950 B1 | 10/2003 | Levin |
| 6,630,086 B1 | 10/2003 | Goral et al. |
| 6,638,252 B2 | 10/2003 | Moulton et al. |
| 6,645,230 B2 | 11/2003 | Whitehurst |
| 6,653,091 B1 | 11/2003 | Dunn et al. |
| 6,669,691 B1 | 12/2003 | Taimisto |
| 6,692,493 B2 | 2/2004 | McGovern et al. |
| 6,693,093 B2 | 2/2004 | Chowdhary et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,719,727 B2 | 4/2004 | Brimhall et al. |
| 6,730,113 B2 | 5/2004 | Eckhardt et al. |
| 6,777,466 B2 | 8/2004 | Eckstein et al. |
| 6,795,728 B2 | 9/2004 | Chornenky et al. |
| 6,801,804 B2 | 10/2004 | Miller et al. |
| 6,819,951 B2 | 11/2004 | Patel et al. |
| 6,827,710 B1 | 12/2004 | Mooney et al. |
| 6,865,416 B2 | 3/2005 | Dev et al. |
| 6,892,099 B2 | 5/2005 | Jaafar et al. |
| 6,897,349 B2 | 5/2005 | Gibbins et al. |
| 6,912,417 B1 | 6/2005 | Bernard et al. |
| 6,927,049 B2 | 8/2005 | Rubinsky et al. |
| 6,929,631 B1 | 8/2005 | Brugger et al. |
| 6,938,668 B2 | 9/2005 | Whicher et al. |
| 6,939,357 B2 | 9/2005 | Navarro et al. |
| 6,962,580 B2 | 11/2005 | Adams et al. |
| 6,962,587 B2 | 11/2005 | Johnson et al. |
| 6,969,381 B2 | 11/2005 | Voorhees |
| 6,972,014 B2 | 12/2005 | Eum et al. |
| 6,994,706 B2 | 2/2006 | Chornenky et al. |
| 6,997,914 B2 | 2/2006 | Smith et al. |
| 7,053,063 B2 | 5/2006 | Rubinsky et al. |
| 7,063,698 B2 | 6/2006 | Whayne et al. |
| 7,070,591 B2 | 7/2006 | Adams et al. |
| 7,130,697 B2 | 10/2006 | Chornenky et al. |
| 7,179,849 B2 | 2/2007 | Terry |
| 7,186,239 B2 | 3/2007 | Woehr |
| 7,211,083 B2 | 5/2007 | Chornenky et al. |
| 7,261,708 B2 | 8/2007 | Raulerson |
| 7,264,858 B2 | 9/2007 | Belliveau et al. |
| 7,267,676 B2 | 9/2007 | Chornenky et al. |
| 7,351,233 B2 | 4/2008 | Parks |
| 7,410,602 B2 | 8/2008 | Davey et al. |
| 7,731,700 B1 | 6/2010 | Schytte |
| 7,785,302 B2 | 8/2010 | Powers |
| 7,947,022 B2 | 5/2011 | Amin et al. |
| 7,959,615 B2 | 6/2011 | Stats et al. |
| 8,021,324 B2 | 9/2011 | Bizup et al. |
| 8,025,639 B2 | 9/2011 | Powers et al. |
| 8,029,482 B2 | 10/2011 | Maniar et al. |
| 8,071,683 B2 | 12/2011 | Mullick et al. |
| 8,177,762 B2 | 5/2012 | Beasley et al. |
| 8,178,620 B2 | 5/2012 | Mullick et al. |
| 8,187,234 B2 | 5/2012 | Weaver et al. |
| 8,202,259 B2 | 6/2012 | Evans et al. |
| 8,257,325 B2 | 9/2012 | Schweikert et al. |
| 8,267,915 B2 | 9/2012 | Daly et al. |
| 8,317,773 B2 | 11/2012 | Appling et al. |
| 8,318,867 B2 | 11/2012 | Mullick et al. |
| 8,338,537 B2 | 12/2012 | Mullick et al. |
| D676,955 S | 2/2013 | Orome |
| 8,377,011 B2 | 2/2013 | Weaver et al. |
| 8,382,723 B2 | 2/2013 | Powers et al. |
| 8,382,724 B2 | 2/2013 | Maniar et al. |
| 2001/0016717 A1 | 8/2001 | Haarala et al. |
| 2001/0044596 A1 | 11/2001 | Jaafar |
| 2001/0047195 A1 | 11/2001 | Crossley |
| 2001/0056266 A1 | 12/2001 | Tallarida et al. |
| 2002/0010491 A1 | 1/2002 | Schoenbach et al. |
| 2002/0055731 A1 | 5/2002 | Atala et al. |
| 2002/0077676 A1 | 6/2002 | Schroeppel et al. |
| 2002/0082559 A1 | 6/2002 | Chang et al. |
| 2002/0091362 A1 | 7/2002 | Maginot et al. |
| 2002/0099323 A1 | 7/2002 | Dev et al. |
| 2002/0138068 A1 | 9/2002 | Watson et al. |
| 2002/0138117 A1 | 9/2002 | Son |
| 2002/0165594 A1 | 11/2002 | Biel |
| 2002/0193831 A1 | 12/2002 | Smith |
| 2003/0009110 A1 | 1/2003 | Tu et al. |
| 2003/0017073 A1 | 1/2003 | Eckhardt et al. |
| 2003/0060856 A1 | 3/2003 | Chornenky et al. |
| 2003/0065355 A1 | 4/2003 | Weber |
| 2003/0088189 A1 | 5/2003 | Tu et al. |
| 2003/0109871 A1 | 6/2003 | Johnson et al. |
| 2003/0130711 A1 | 7/2003 | Pearson et al. |
| 2003/0135168 A1 | 7/2003 | Benchetrit |
| 2003/0170898 A1 | 9/2003 | Gundersen et al. |
| 2003/0194433 A1 | 10/2003 | Hei et al. |
| 2003/0203991 A1 | 10/2003 | Schottman et al. |
| 2003/0208200 A1 | 11/2003 | Palanker et al. |
| 2003/0220628 A1 | 11/2003 | Klisch et al. |
| 2003/0225360 A1 | 12/2003 | Eppstein et al. |
| 2004/0019371 A1 | 1/2004 | Jaafar et al. |
| 2004/0034398 A1 | 2/2004 | Eckhardt et al. |
| 2004/0059389 A1 | 3/2004 | Chornenky et al. |
| 2004/0064086 A1 | 4/2004 | Gottlieb et al. |
| 2004/0068241 A1 | 4/2004 | Fischer |
| 2004/0068251 A1 | 4/2004 | Chan et al. |
| 2004/0068315 A1 | 4/2004 | Chandrasekaran et al. |
| 2004/0073171 A1 | 4/2004 | Rogers et al. |
| 2004/0076582 A1 | 4/2004 | Dimatteo et al. |
| 2004/0116965 A1 | 6/2004 | Falkenberg |
| 2004/0121175 A1 | 6/2004 | Flexman et al. |
| 2004/0131863 A1 | 7/2004 | Belliveau et al. |
| 2004/0133173 A1 | 7/2004 | Edoga et al. |
| 2004/0146877 A1 | 7/2004 | Diss et al. |
| 2004/0153057 A1 | 8/2004 | Davison |
| 2004/0167463 A1 | 8/2004 | Zawacki et al. |
| 2004/0171747 A1 | 9/2004 | Zhong |
| 2004/0199128 A1 | 10/2004 | Morris et al. |
| 2004/0204691 A1 | 10/2004 | Yashiro et al. |
| 2004/0243103 A1 | 12/2004 | King et al. |
| 2004/0243107 A1 | 12/2004 | Macoviak et al. |
| 2004/0267189 A1 | 12/2004 | Mavor et al. |
| 2005/0010275 A1 | 1/2005 | Sahatjian et al. |
| 2005/0013988 A1 | 1/2005 | Fu et al. |
| 2005/0033237 A1 | 2/2005 | Fentress et al. |
| 2005/0043726 A1 | 2/2005 | McHale et al. |
| 2005/0049541 A1 | 3/2005 | Behar et al. |
| 2005/0059958 A1 | 3/2005 | Lessard et al. |
| 2005/0104255 A1 | 5/2005 | Mejlhede et al. |
| 2005/0119724 A1 | 6/2005 | Phaneuf et al. |
| 2005/0124980 A1 | 6/2005 | Sanders |
| 2005/0131356 A1 | 6/2005 | Ash et al. |
| 2005/0137580 A1 | 6/2005 | Raulerson et al. |
| 2005/0143817 A1 | 6/2005 | Hunter et al. |
| 2005/0165393 A1 | 7/2005 | Eppstein |
| 2005/0171490 A1 | 8/2005 | Weaver et al. |
| 2005/0171510 A1 | 8/2005 | DiCarlo et al. |

(56) References Cited

U.S. PATENT DOCUMENTS

| | | |
|---|---|---|
| 2005/0171523 A1 | 8/2005 | Rubinsky et al. |
| 2005/0171574 A1 | 8/2005 | Rubinsky et al. |
| 2005/0176893 A1 | 8/2005 | Rana et al. |
| 2005/0182352 A1 | 8/2005 | DiMatteo et al. |
| 2005/0182462 A1 | 8/2005 | Chornenky et al. |
| 2005/0192546 A1 | 9/2005 | Griego et al. |
| 2005/0197619 A1 | 9/2005 | Rule et al. |
| 2005/0216074 A1 | 9/2005 | Sahatjian et al. |
| 2005/0240080 A1 | 10/2005 | Diekmann et al. |
| 2005/0256461 A1 | 11/2005 | DiFiore et al. |
| 2005/0261636 A1 | 11/2005 | Rome et al. |
| 2005/0261672 A1 | 11/2005 | Deem et al. |
| 2005/0288730 A1 | 12/2005 | Deem et al. |
| 2006/0004325 A1 | 1/2006 | Hamatake et al. |
| 2006/0015086 A1 | 1/2006 | Rasmussen et al. |
| 2006/0015147 A1 | 1/2006 | Persson et al. |
| 2006/0025760 A1 | 2/2006 | Podhajsky |
| 2006/0052757 A1 | 3/2006 | Fischer et al. |
| 2006/0064159 A1 | 3/2006 | Porter et al. |
| 2006/0079883 A1 | 4/2006 | Elmouelhi et al. |
| 2006/0100592 A1 | 5/2006 | Eliasen |
| 2006/0121610 A1 | 6/2006 | Rubinsky et al. |
| 2006/0178648 A1 | 8/2006 | Barron et al. |
| 2006/0189922 A1 | 8/2006 | Amarasinghe et al. |
| 2006/0212078 A1 | 9/2006 | Demarais et al. |
| 2006/0217703 A1 | 9/2006 | Chornenky et al. |
| 2006/0247584 A1 | 11/2006 | Sheetz et al. |
| 2006/0264752 A1 | 11/2006 | Rubinsky et al. |
| 2006/0264833 A1 | 11/2006 | Moulton |
| 2006/0293730 A1 | 12/2006 | Rubinsky et al. |
| 2007/0037891 A1 | 2/2007 | Esfand et al. |
| 2007/0043345 A1 | 2/2007 | Davalos et al. |
| 2007/0060989 A1 | 3/2007 | Deem et al. |
| 2007/0078385 A1 | 4/2007 | Accisano et al. |
| 2007/0078391 A1 | 4/2007 | Wortley et al. |
| 2007/0118069 A1 | 5/2007 | Persson et al. |
| 2007/0161940 A1 | 7/2007 | Blanchard et al. |
| 2007/0167925 A1 | 7/2007 | Jacqmein |
| 2007/0191771 A1 | 8/2007 | Moyer |
| 2007/0219497 A1 | 9/2007 | Johnson et al. |
| 2007/0239099 A1 | 10/2007 | Goldfarb et al. |
| 2007/0255237 A1 | 11/2007 | Lobl et al. |
| 2007/0260221 A1 | 11/2007 | Chesnin |
| 2007/0270754 A1 | 11/2007 | Soderholm et al. |
| 2007/0287967 A1 | 12/2007 | Hekmat et al. |
| 2008/0052786 A1 | 2/2008 | Lin et al. |
| 2008/0108975 A1 | 5/2008 | Appling et al. |
| 2008/0154186 A1 | 6/2008 | Appling et al. |
| 2008/0228253 A1 | 9/2008 | Mullick et al. |
| 2008/0234659 A1 | 9/2008 | Cheng et al. |
| 2008/0294111 A1 | 11/2008 | Tal et al. |
| 2008/0306465 A1 | 12/2008 | Bailey et al. |
| 2009/0036768 A1 | 2/2009 | Seehusen et al. |
| 2009/0118683 A1* | 5/2009 | Hanson ............. A61M 39/0208 604/288.01 |
| 2009/0171319 A1 | 7/2009 | Guo et al. |
| 2009/0171436 A1 | 7/2009 | Casanova et al. |
| 2009/0204074 A1 | 8/2009 | Powers et al. |
| 2009/0211968 A1 | 8/2009 | Ho et al. |
| 2009/0216216 A1 | 8/2009 | Powers et al. |
| 2009/0306606 A1 | 12/2009 | Lancette et al. |
| 2009/0326515 A1 | 12/2009 | Kagan |
| 2010/0049147 A1 | 2/2010 | Tanikawa et al. |
| 2010/0106094 A1 | 4/2010 | Fisher et al. |
| 2010/0191165 A1 | 7/2010 | Appling et al. |
| 2011/0009799 A1 | 1/2011 | Mullick et al. |
| 2011/0071500 A1 | 3/2011 | Lareau |
| 2011/0098662 A1 | 4/2011 | Zinn |
| 2011/0160673 A1 | 6/2011 | Magalich et al. |
| 2011/0184353 A1 | 7/2011 | DeMaria |
| 2011/0207893 A1 | 8/2011 | Mullick et al. |
| 2011/0264058 A1 | 10/2011 | Linden et al. |
| 2012/0053512 A1 | 3/2012 | Muse |
| 2012/0095440 A1 | 4/2012 | Islam |
| 2012/0148774 A1 | 6/2012 | Mullick et al. |
| 2012/0184925 A1 | 7/2012 | Grant |
| 2012/0220724 A1 | 8/2012 | Mullick et al. |
| 2012/0232472 A1 | 9/2012 | Bhagchandani et al. |
| 2013/0060200 A1 | 3/2013 | Dalton et al. |
| 2013/0102962 A1* | 4/2013 | Shih ................. A61M 5/14276 604/123 |

FOREIGN PATENT DOCUMENTS

| | | |
|---|---|---|
| EP | 0670169 | 7/1990 |
| EP | 0935482 A1 | 8/1999 |
| WO | WO9639531 A1 | 12/1996 |
| WO | WO9818506 | 5/1998 |
| WO | WO0020554 A1 | 4/2000 |
| WO | WO0107583 A1 | 2/2001 |
| WO | WO0107584 A1 | 2/2001 |
| WO | WO0107585 A1 | 2/2001 |
| WO | WO0181533 A1 | 11/2001 |
| WO | WO0187416 | 11/2001 |
| WO | WO02102421 | 12/2002 |
| WO | WO2004037341 A2 | 5/2004 |
| WO | WO2005065284 A2 | 5/2004 |

OTHER PUBLICATIONS

Chand, et al, Use of Vascular Ports for Long-Term Apheresis in Children, J Vasc Interv Radiol 2015, 26: 1669-1672.

Shrestha, et al, Use of a Dual Lumen Port for Automated Red Cell Exchange in Adults with Sickle Cell Disease, Journal of Clinical Apheresis, 2015.

Sails et al., Can Peripherally Inserted Central Catheters be Used for Contrast Injection with a CT Power Injector?, JVIR vol. 13, Issue 2, Feb. 2002, Supplement S1.

Garland et al., Measurement of Extravascular Lung Water in Hemodialysis Patients Using Blood Ultrasound Velocity and Optical Density Dilution, American Society of Artificial Internal Organs Journal, 2002, pp. 398-403.

Teichgraber et al., Central Venous Access Catheters: Radiological Management of Complications, Cardiovascular and Interventional Radiology, Jul. 31, 2003, pp. 321-333.

Glickman et al., Challenges of hemodialysis access for high risk patients: Impact of mesenteric vein bioprosthetic graft, The Journal of Vascular Access, 2003 pp. 73-80.

Choi et al., Peritoneal Dialysis, Medicine, 2003, pp. 70-73.

Scher et al., Alternative Graft Materials for Hemodialysis Access, Seminars in Vascular Surgery, vol. 17, No. 1, Mar. 2004, pp. 19-24.

Wentling, Hemodialysis Catheters: Materials, Design and Manufacturing, Hemodialysis Vascular Access and Peritoneal Dialysis Access, vol. 142, 2004, pp. 112-127.

Siegman-Igra et al, Diagnosis of Vascular Catheter-Related Bloodstream Infection: a Meta-Analysis, Journal of Clinical Microbiology, vol. 35, No. 4, Apr. 1997, pp. 928-936.

Kindgen-Milles et al, Assessment of Temporary Dialysis Catheter Performance on the Basis of Flow and Pressure Measurements In Vivo and In Vitro, ASAIO Journal, 2007, pp. 351-356.

Spector et al., Clininical Outcome of the Tal Palindrome Chronic Hemodialysis Catheter: Single Institution Experience, Journal of Vascular Interventional Radiology, vol. 19, No. 10, 2008, pp. 1434-1438.

Nael et al., Endovascular Management of Central Thoracic Veno-Occlusive Diseases in Hemodialysis Patients: A Single Institutional Experience in 69 Consecutive Patients, Journal of Vascular Interventional Radiology, vol. 20, No. 1, 2009, pp. 46-51.

Saad et al., Dual-Tract Transhepatic U-shaped Hemodialysis Inferior Vena Cava Catheter: A Feasibility Study in a Swine Model, Journal of Vascular Interventional Radiology, vol. 20, No. 12, Dec. 2009, pp. 1625-1631.

Witowski et al., Peritoneal Dialysis: A Biological Membrane with a Nonbiological Fluid, Biology of Peritoneal Membrane, 2009, pp. 27-34.

Cavallini et al., Substituting Citrate for Lactate in Peritoneal Dialysis Fluid Improves Ultrafiltration in Rats, Peritoneal Dialysis International, vol. 29, Jan. 2009, pp. 36-43.

(56) References Cited

OTHER PUBLICATIONS

Chan et al., Tunneled Dialysis Catheters: Recent Trends and Future Directions, Advances in Chronic Kidney Disease, vol. 16, No. 5, Sep. 2009, pp. 386-395.
Olinger et al., Acute clinical hypocalcemic myocardial depression during rapid blood transfusion and postoperative hemodialysis: A preventable complication, The Journal of Thoracic and Cardiovascular Surgery, vol. 72, No. 4, Oct. 1976, pp. 503-511.
McCarthy, et al, The Use of a Flow Rate Injetor for Contrast-Enhanced CT, Radiology, 1984, 151:800.
Ireland, et al, Safety and Convenience of a Mechanical Injector Pump for Conorary Angiography, Catheterization and Cardiovascular Diagnosis, 1989, 16:199-201.
Miles, et al, Safe use of an Intravenous Power Injector for CT: Experience and Protocol, RSNA, 1990, pp. 69-70.
Carlson, et al, Safety Considerations in the Power Injection of Contrast Media Via Central Venous Catheters During Computed Tomographic Examinations, Investigative Radiology vol. 27, 1992, pp. 337-340.
Steinbach, et al, Breast Implants, Common Complications, and Concurrent Breast Disease, RadioGraphics 1993, 13:95-118.
Vergara, Adverse Reactions to Contrast Media in CT: Effects of Temperature and Ionic Property, Radiology 1996, 199:363-366.
Herts, et al, Power Injection of Contrast Material through Central Venous Catheters for CT: In Vitro Evaluation, Radiology 1996, 200:731-735.
Kaste, et al, Safe Use of Power Injectors with Central and Peripheral Venous Access Devices for Pediatric CT, Pediatr Radiol, 1996, 36:499-501.
Urquiola, et al, Using Lead Foil as a Radiopaque Marker for Computerized Tomography Imaging when Implant Treatment Planning, Journal of Prosthetic Dentistry vol. 77 No. 2, 1997, pp. 227-228.
Hills, et al, Experience with 100 Consecutive Central Venous Access Arm Ports Placed by Interventional Radiologists, JVIR 1997, 8:983-989.
Ruess, et al, In-line Pressures Generated in Small-Bore Central Venous Catheters During Power Injection of CT Contrast Media, Radiology 1997, 203:625-629.
Blot, et al, Accuracy of Totally Implanted ports, tunnelled, single and multiple-lumen contral venous catheters for measurement of central venous pressure, Intensive Care Med, 2000, pp. 1837-1842.
Biffi, et al, A Randomized, Prospective Trial of Central Venous Ports Connected to Standard Open-Ended or Groshong Catheters in Adult Oncology Patients, American Cancer Society, 2001, pp. 1204-1212.
Funaki, Central Venous Access: A Primer for the Diagnostic Radiologist, AJR: 179, 2002, pp. 309-318.
Teichgraber, et al, Central Venous Access Catheters: Radiological Management of Complications, Cardiovasc Intervent Radiol, 2003, 26:321-333.
Costa, More Than Skin Deep: An Overview of Iodinated Contrast Media, JAVA vol. 8 No. 4, 2003, pp. 34-39.
Scher, et al, Alternative Graft Materials for Hemodialysis Access, Seminars in Vascular Surgery, vol. 17 No. 1, 2004, pp. 19-24.
Abstracts of the World Apheresis Association 10th Congress, Jornal of Clinical Apheresis, 2004, 18: 20-58.
Sanelli, Safety and Feasibility of Using a Central Venous Catheter for Rapid Contrast Injection Rates, AJR 183, 2004, pp. 1829-1834.
Swindle, et al, Vascular Access Port Usage in Large Animal Species, Contemporary Topics, 2005 vol. 44 No. 27 pp. 7-17.
Gebauer, Contrast Media Pressure Injectoin Using a Portal Catheter System—Results of an in Vitro Study, ROFO 2005, pp. 1417-1423.
Hou, et al, Comparisons of Outcomes and Survivals for Two Central Venous Access Port Systems, Journal of Surg Oncology, 2005, 91:61-66.
Swerdlow, Red Cell Exchange in Sickle Cell Disease, American Society of Hematology, 2006, pp. 48-53.
Supplement to Imaging Economics, CIN Strategies: Anticipate, Manage, Prevent, 2007, S1-S18.
Medtronic Synchromed II & Synchromed EL Priming Bolus Reference Card, 2007.
International Search Report PCT-US-99-03982_ISR dated Jul. 14, 1999.
International Search Report PCT-US-08-061447_IPRP dated Sep. 16, 2008.
International Search Report PCT-US-08-061447_ISR dated Sep. 16, 2008.
International Search Report PCT-US-12-030110_ISR dated Jul. 11, 2012.
International Search Report PCT-US-08-078976 WOSA dated Apr. 3, 2009.
International Search Report PCT-US-08-078976 IPRP dated Apr. 7, 2010.
International Search Report PCT-US-08-010520 IPRP dated Mar. 9, 2010.
International Search Report PCT-US-03-033373 ISR dated Mar. 15, 2004.
International Search Report PCT-US-08-010520 ISR dated Feb. 24, 2009.
International Search Report PCT-US-08-010520 WOSA dated Feb. 24, 2009.

* cited by examiner (SINGLE PROFILE)

(OVERLAPPING PROFILE)

HIGH-FLOW PORT AND INFUSION NEEDLE SYSTEMS

CROSS-REFERENCE TO RELATED APPLICATIONS

This application claims priority to U.S. provisional application No. 61/925,287 filed on Jan. 9, 2014, of which is incorporated herein by reference in its entireties.

FIELD OF THE INVENTION

The present invention relates generally to the field of vascular access ports. More specifically, the present invention relates to multi-reservoir port and infusion needle systems that support high-flow applications such as hemodialysis and apheresis.

BACKGROUND OF THE INVENTION

Multi-lumen catheters are commonly used for extracorporeal procedures in which blood is removed from the vascular system through an aspiration lumen, treated and returned to circulation through an infusion lumen. Apheresis is one example an extracorporeal procedure in which a patient's blood is removed from the vascular system, passed through a machine that removes specific blood components (e.g., plasma, red blood cells, white blood cells and/or platelets etc.) and then returned to circulation. Apheresis procedures generally last from one to four hours, although these times may vary depending on the procedure being performed, the medical condition being treated, the size of the patient and the type of machine being used. The number of treatments also varies based on the procedure being performed. Some procedures, such as red blood cell exchange, are only performed once. In other situations the patient is re-evaluated after two or three procedures to determine if they are responding to the treatment. Certain diseases require a pre-set treatment schedule that may include, for example, five procedures over the course of two weeks. Other procedures require the patient to follow a routine schedule of treatment that may vary from multiple times per week to once per month. Examples of apheresis procedures that require frequent treatments include plasma exchange (e.g., the removal of harmful substances from the blood plasma and subsequent replacement with saline, normal serum albumin or fresh frozen plasma); low density lipoprotein (LDL) apheresis (e.g., to treat familial hypercholesterolemia); photopheresis (e.g., to treat graft-versus-host disease; cutaneous T-cell lymphoma; or heart transplant rejection); allo- and autoantibody removal (e.g., to treat autoimmune disease; hemophilia; or transplant rejection); leukocytapheresis (e.g., to remove malignant white blood cells in leukemia) and thrombocytapheresis (e.g., to treat essential thrombocythemia; or polycythemia vera). Hemodialysis is another example of an extracorporeal procedure in which waste products, such as creatinine, urea, potassium, phosphate and/or free water, are removed from the blood of a patient whose kidneys are in a state of renal failure. In general, hemodialysis treatments are required once a patient has lost 85 to 90 percent of their kidney function. A typical treatment schedule requires performing hemodialysis 3 times a week, although patients who have retained substantial residual kidney function might only require sessions twice-a-week. Larger patients, or patients who have difficulties with fluid overload, may require four hemodialysis sessions per week are often prescribed for larger patients. Short daily home hemodialysis treatments may be performed as frequently as five to seven times per week. While both procedures require the continued re-circulation of blood through an external apparatus, the flow rates required for hemodialysis generally exceed those required for apheresis. For example, hemodialysis typically requires flow rates in the range 300-400 ml/min, but can sometimes exceed 800 ml/min. By contrast, the flow rates required for apheresis procedures can range from 30-60 ml/min (e.g., red blood cell exchange) to 150 ml/min (e.g., plasma exchange).

Medical professionals often prefer the use of implantable ports over peripherally inserted central catheters (i.e., PICCs) for procedures such as apheresis and hemodialysis that require repeated and/or prolonged access to the vascular system. One advantage of implantable ports is that they are completely indwelling, and therefore minimize the risk of infection, especially in patients requiring chronic care. Implantable ports are also more amenable to patients with active lifestyles since their relatively low profile allows them to be easily hidden from view. Ports are typically implanted in the patient's chest and connected to a catheter having a distal tip positioned at the point of treatment. For example, for many medical procedures the catheter tip is positioned at the junction of the superior vena cava and the right atrium. Implantable ports generally include a reservoir (i.e., chamber) in fluid communication with a catheter. The reservoir is typically covered by a needle-penetrable and self-sealing elastomeric septum. The self-sealing septum allows the reservoir to be accessed by puncturing both the patient's skin and the septum with a needle, for example, to infuse and/or aspirate fluid to and from the distal tip of the catheter.

For medical procedures that require multi-lumen access to the vascular system it is common for two ports to be implanted within the patient. While a variety of arrangements are possible, it is most common for one port to be implanted within the patient's left arm and the other port implanted within the right arm. In addition to the increased cost associated with implanting two ports, the separate invasive procedures dramatically increases patient discomfort and the likelihood of negative outcomes such as infection. These problems may be avoided by implanting a multi-reservoir port, which allows the administration of fluid through one reservoir and aspiration of fluid through a separate reservoir. While multi-reservoir ports are more cost-efficient, minimize patient discomfort and decrease patient exposure, they do have drawbacks.

Since fluid flows through a conventional multi-reservoir port (including the catheter) as a continuous stream, it is important that pressure on the aspiration side remains equal (i.e., balanced) to the pressure on the infusion side. With the power source for fluid flow provided by the apheresis or hemodialysis machine, fluid is essentially pulled through the aspiration side under negative pressure and pushed through the infusion side under positive pressure. This requires fluid on the aspiration side to travel a greater distance to reach the power source than fluid on the infusion side, resulting in the formation of high intraluminal negative pressures. These negative pressures force the lumen of the aspiration catheter to collapse or constrict, thereby restricting the flow of fluid throughout the entire system. To avoid harming the patient, automated apheresis and hemodialysis machines are designed to set-off pressure alarms when high intraluminal pressure is detected.

To maintain the proper pressure balance within multi-reservoir port systems, medical professionals typically access the aspiration reservoir of conventional multi-reservoir port systems with a 16 gauge needle. The large inner diameter of the 16 gauge needle is preferred over smaller 18 or 19 gauge needles because they allow fluid to flow into the aspiration reservoir under minimal pressure such that pressure alarms are not set-off. Due to its large inner diameter, a trocar is inserted into the lumen of the 16 gauge needle to prevent coring of the elastomeric septum covering the aspiration reservoir. Unfortunately, the size and shape of standard 16 gauge trocar needles creates large puncture sites within the elastomeric septum. Repeated overlapping punctures by the 16 gauge trocar eventually result in the formation of leakage sites within the septum, ultimately rendering the port unsuitable for safe and reliable use.

As evidenced by the competing interests of maintaining septum integrity and avoiding high intraluminal negative pressure, there is a continuing need for multi-reservoir port and non-coring needle systems that support high-flow applications with minimal impact on the puncture life of the elastomeric septum.

SUMMARY OF THE INVENTION

The present invention relates generally to multi-reservoir port, catheter and non-coring needle systems that support high-flow applications such as hemodialysis and apheresis. In one aspect, the present invention relates to improved port, catheter and needle systems that provide, both alone and in combination, optimal flow rates and septum puncture life with minimal intraluminal pressure.

In one embodiment, the present invention relates to a high flow multi-reservoir port assembly, comprising a vascular access port that includes a housing defining first (i.e., aspiration) and second (i.e., infusion) reservoirs. A first septum is mounted within the housing to seal the first reservoir, and a second septum is mounted within the housing to seal the second reservoir. The first and second septa (plural) are configured to be penetrable by a needle, and self-sealing after the needle is withdrawn. An inlet stem with an inlet lumen is in fluid communication with the first reservoir, and an outlet stem with an outlet lumen is in fluid communication with the second reservoir. The inlet and outlet stems are in fluid communication with a dual-lumen catheter that includes a proximal end, a distal end and first and second lumens extending therebetween. The catheter includes a smooth outer surface having a substantially circular outer diameter. The inlet stem is dimensioned to receive the first lumen at the proximal end of the catheter, and the outlet stem is dimensioned to receive the second lumen at the proximal end of the catheter. The first and second septa comprise an elastomeric material, including, for example, a multi-durometer material. The elastomeric material is self-sealing. The multi-durometer elastomeric material may comprise a first layer with a first durometer and a second layer with a second durometer. For example, the durometer of the material of the first layer may be less than the durometer of the material of the second layer. The first layer may be disposed above (i.e., on top of) the second layer. Alternatively, the first layer may surround the second layer. The first layer may also be disposed both above and below the second layer, such that the second layer is effectively sandwiched between two first layers. The first and second layers may include a variety of thicknesses. For example, the thickness of the second layer may be greater than the thickness of the first layer. Alternatively, the thickness of the first and second layers may be substantially the same. The first lumen of the catheter comprises a first inner diameter, and the second lumen of the catheter comprises a second inner diameter, wherein the second inner diameter is smaller than the first inner diameter. The first and second lumens of the catheter may include a variety of shapes. For example, the first inner diameter may define a substantially oval shape, while the second inner diameter may define a substantially concave shape. The first and second lumens of the catheter also define respective first and second openings at the distal end of the catheter. The openings do not necessarily terminate at the same location along the length of the catheter. For example, the first opening may be located proximal to the second opening. That is, the second opening may be located at or near the distal tip of the catheter, while the first opening is located at a position closer to the port. The first opening may also be substantially perpendicular to the second opening.

In another aspect, the present invention relates to a needle assembly, comprising at least one infusion needle and at least two aspiration needles. The at least one infusion needle is configured to penetrate the second septum of the second reservoir, while the at least two aspiration needles are configured to penetrate the first septum of the first reservoir (described above). The aspiration and infusion needles are, therefore, in fluid communication with the aspiration and infusion reservoirs, respectively. The at least one infusion needle and the at least two aspiration needles may include non-coring (i.e., Huber) needles. Needles of any size (i.e., gauge) may be used, for example, both the infusion and aspiration needles may be at least 19 gauge. To establish optimal fluid flow, the at least two aspiration needles may include openings that face in substantially opposite directions. Alternatively, the openings of the at least two aspiration needles may be configured such that they both face the inlet port of the aspiration reservoir. The at least two needles may be attached to each other, at for example, a y-site. The infusion needle may also include an opening configured to face the outlet port of the infusion reservoir. The at least two aspiration needles and at least one infusion needle allow the aspiration and infusion reservoirs to be in fluid communication with a blood circulation apparatus, such as an apheresis or hemodialysis machine.

In another embodiment, the present invention contemplates kits for the practice of the methods of this invention. The kits may include one or more containers containing a multi-reservoir implantable port, an aspiration needle assembly, an infusion needle assembly and catheter.

As used herein, "coring" refers to any portion of the septum that is forced into the shaft of a needle as the needle tip advances through the septum body. Septum coring produces small, detached particles that may become trapped in the cardiovascular system of the patient. In addition to potentially harming the patient, these particles can obstruct fluid flow through the needle assemblies and/or outlet stem of the multi-reservoir port. While a septum is capable of withstanding a certain number of coring events, continued coring creates a series of small passageways that extend through the body of the septum and eventually lead to various forms of septum failure. To at least partially address this problem, non-coring (e.g., Huber) needles are preferably used in conjunction with aspiration and infusion assemblies for accessing port reservoirs. Unlike traditional hypodermic needles, non-coring Huber needles pierce the septum in a knife-like fashion, thereby facilitating the resealing of the septum so that the aforementioned problems are largely averted.

As used herein, "trocar" refers to a surgical instrument having a sharpened point used to puncture a percutaneous surface for a variety of minimally invasive medical applications. In one embodiment, the body of the trocar includes a hollow tube through which a variety of medical instruments can be inserted into a patient's body. Alternatively, the body of the trocar can include a solid shaft, or sealed tube, dimensioned to fit within and reversibly occlude the lumen of a needle. The pointed tip of the trocar extends beyond, or is substantially flush with, the pointed end of the needle. Once the target surface (e.g., the skin, septum etc.) has been penetrated, the trocar is removed such that the lumen of the needle remains in fluid contact with the selected reservoir, chamber or body site.

As used herein, "durometer" refers to the measurement of a material's resistance to permanent indentation (i.e., hardness), and is typically used in reference to polymers, elastomers rubbers and the like. A material's durometer value can be determined by measuring the depth of an indentation in the material created by a given force on a standardized pressure foot. The depth of the indentation within the material is dependent on a variety of factors, including the density of the material, its viscoelastic properties, the shape of the pressure foot and the duration of the test.

As used herein, a "staggered tip" refers to a dual-lumen catheter that prevents fluid recirculation by positioning the entry site of the aspiration lumen away from the exit site of the infusion lumen (located at or near the catheter tip). Staggered-tip catheter designs are known in the art, including for example U.S. Pat. Nos. 8,317,773 and D603,044, herein incorporated by reference. The staggered tip design ensures that treated blood exiting the infusion lumen is carried away from the catheter tip as it re-enters circulation.

Other aspects, features, and advantages of the present invention are outlined in the detailed description, drawings, and claims.

BRIEF DESCRIPTION OF THE DRAWINGS

Non-limiting embodiments of the present disclosure will be described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure.

DETAILED DESCRIPTION OF THE INVENTION

Figure 1A:
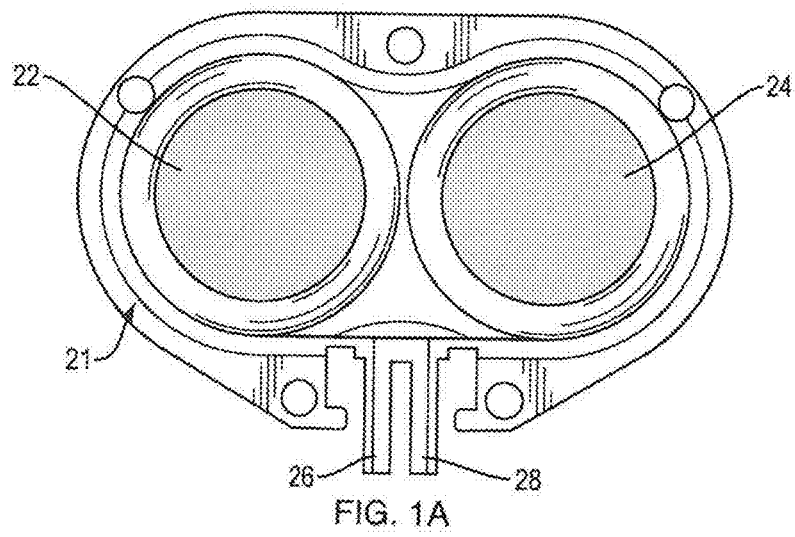
FIGS. 1A-C provide a top view of a multi-reservoir port system, in accordance with one embodiment of the present invention.

The present invention may be further understood with reference to the following description and the appended drawings, wherein like elements are referred to with the same reference numerals. The systems and methods of the present invention relate to multi-reservoir port, catheter and needle systems that support high-flow applications such as hemodialysis and apheresis. However, those skilled in the art will understand that the present invention is equally pertinent to a wide range of applications that benefit from the implantation of multi-reservoir ports with self-sealing septa, and which are accessible by a corresponding non-coring needle assembly.

As described herein, the present invention improves upon various components of conventional implantable port, needle-assembly and catheter designs to provide a system capable of maintaining balanced intraluminal fluid pressure required for high flow applications, without a corresponding decrease in septum puncture life. These advantages include 1) needle designs and configurations that provide optimal fluid flow and minimize damage to the septum, 2) dual-durometer septum designs and configurations that optimize self-sealing and minimize coring and 3) dual-lumen catheter designs and configurations that facilitate low pressure fluid flow within the aspiration lumen and prevent lumen constriction/collapsing. The cumulative effect that results from combining any, or all, of these improvements into a single system exceeds the improvements realized by an individually improvement alone. These improvements provide direct and immediate benefits to both the patient and medical professional. For example, the multi-reservoir ports decrease patient discomfort during implantation by requiring only a single invasive procedure, and are easier to conceal than separate single-reservoir ports implanted at different locations within the body. Patient discomfort is also decreased during treatment by limiting needle punctures through the skin to a single access site. Additionally, the ability to withstand a high number of needle punctures without septum failure allows expensive and invasive port replacement procedures to be postponed, or avoided altogether. This represents a significant savings in terms of medical costs, as well patient discomfort and risk exposure to.

Figure 1B:
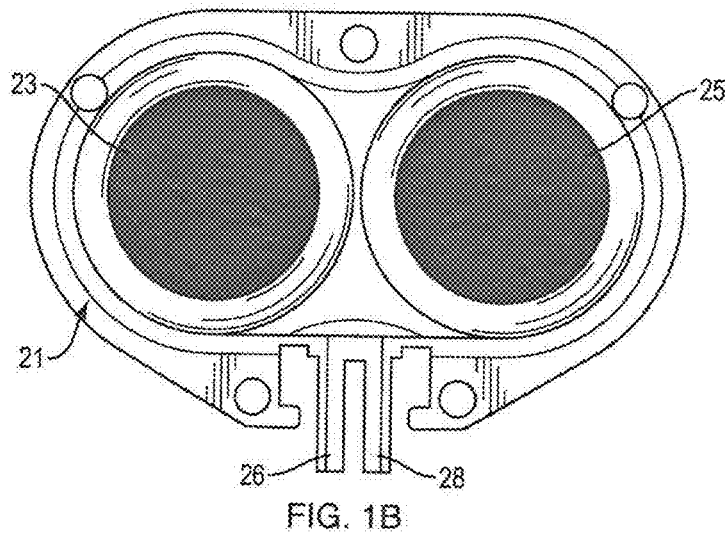
Figure 1C:
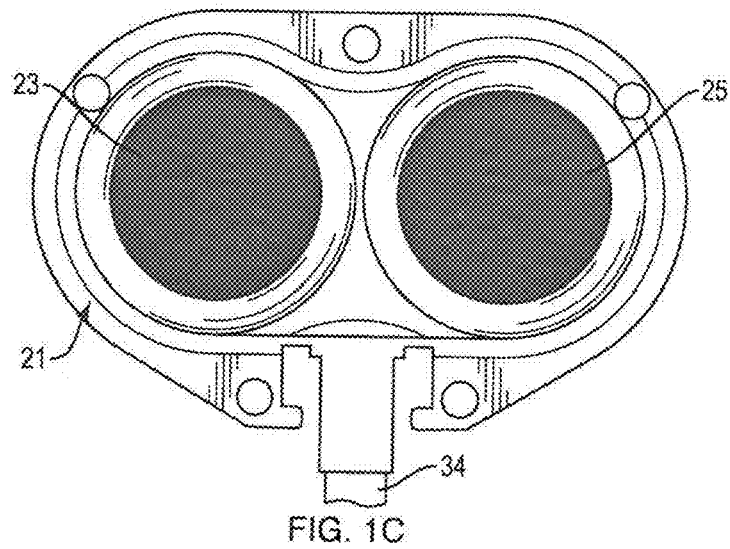

Multi-reservoir ports typically used in situations that require multi-lumen access to the vascular system. Examples of multi-reservoir ports, including the manner of fabrication and method of use are described in U.S. Patent Publication Nos. 20130150811 and 20090118683, each of which is assigned to Angiodynamics, Inc. of Latham, N.Y., and are fully incorporated herein by reference. Referring to FIG. 1, in one embodiment the present invention provides a multi-reservoir port 20 of the present invention includes a housing 21 that defines an aspiration reservoir 22 and an infusion reservoir 24 (i.e., first and second reservoirs, respectively). The aspiration 22 and infusion 24 reservoirs are covered and sealed by a first 23 and second 25 elastomeric septum, respectively. Each septum generally comprises a flexible membrane selected for its ability to continually re-seal the port reservoir following repeated punctures by a needle. An inlet stem 26 that defines an inlet lumen (not shown) is in fluid communication with the aspiration reservoir 22, and an outlet stem 28 that defines an outlet lumen (not shown) is in fluid communication with the infusion reservoir 24. The inlet 26 and outlet 28 stems are dimensioned to receive the proximal end 32 (i.e., proximal tip) of a dual-lumen catheter 30.

Figure 2A:
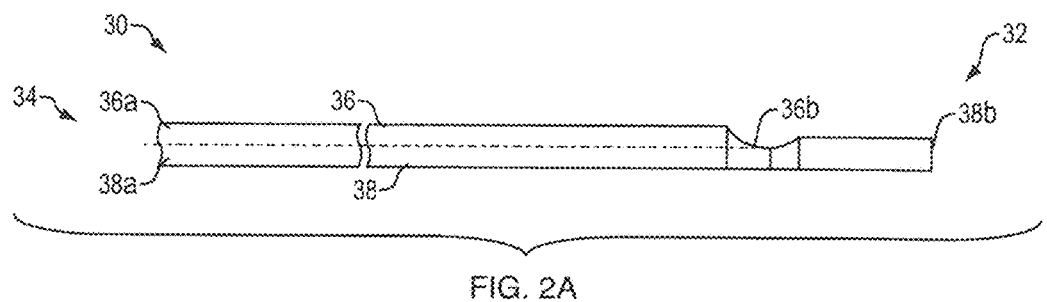
FIGS. 2A-B provides a schematic side-view of a staggered-tip catheter designs, in accordance with one embodiment of the present invention.
Figure 2B:
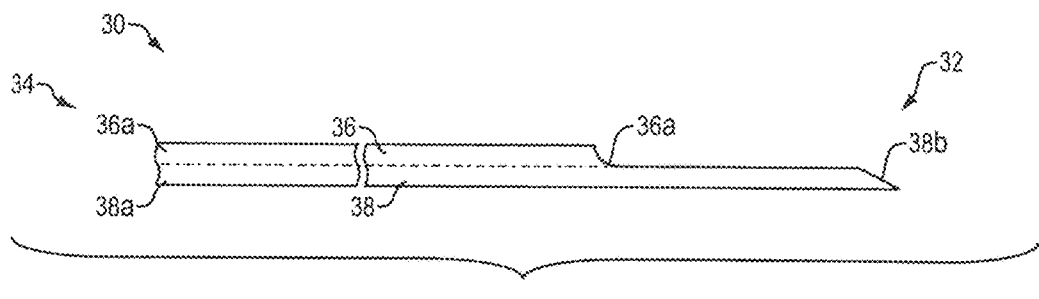

Referring to FIG. 2, in one embodiment the dual-lumen catheter includes a proximal end 32 and a distal end 34, with aspiration 36 and infusion 38 lumens (i.e., first and second lumens, respectively) extending therebetween. The aspiration lumen 36 at the distal end 34 of catheter 30 includes an opening 36a dimensioned to receive the inlet stem 26 of the multi-reservoir port 20 (FIG. 1C), such that the proximal end 32 of the catheter 30 is in fluid communication with the aspiration reservoir 22. Similarly, the infusion lumen 38 at the distal end 34 of catheter 30 includes an opening 38a dimensioned to receive the outlet stem 28 of the multi-reservoir port 20 (FIG. 1C), such that the proximal end 32 of the catheter 30 is in fluid communication with the infusion reservoir 24. The proximal end 32 of the dual-lumen catheter 30 includes a proximal opening 36b of the aspiration lumen 36 that is located distal to the proximal opening 38b of the infusion lumen 38. Additional examples of dual-lumen catheters are described in U.S. Pat. Nos. 7,410,602 and 8,317,773, each of which is assigned to Angiodynamics, Inc. of Latham, N.Y., and are fully incorporated herein by reference.

Figure 3:
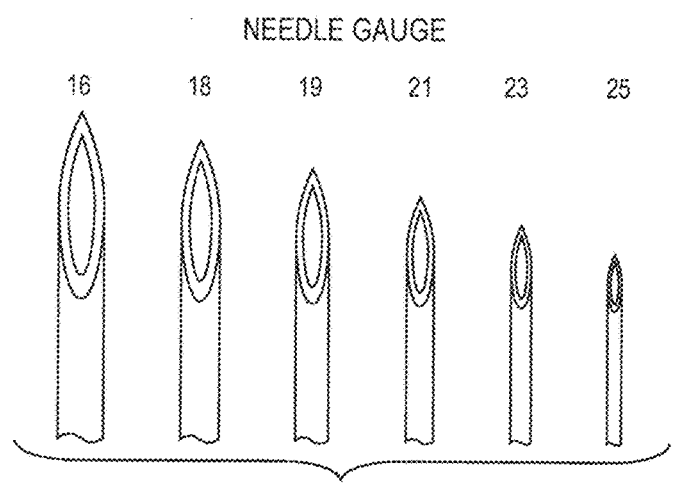
FIG. 3 provides a side-by-side comparison of the size of various gauge needles known in the art.

Medical procedures such as apheresis or hemodialysis require the septa covering the aspiration and infusion reservoirs to be frequently and repetitively punctured with a needle. The cumulative damage resulting from these needle penetrations gradually degrades the elastomeric septum until it is eventually unable to re-seal itself. The number of punctures that a septum can withstand depends on the size of the port, the type of elastomeric material, the durometer of the elastomeric material and the size of needle(s). FIG. 3 provides a side-by-side comparison of the relative sizes of standard needles used for various medical procedures. As would be expected, larger gauge needles cause more damage and decrease the "puncture life" or "stick life" of the septum. A typical septum is able to withstand approximately 50-100 punctures by a 16 gauge needle before its integrity is compromised to the point that it must be replaced. By contrast, the same septum can withstand upwards of 500 punctures by a standard 19 gauge needle. Thus, while a 16 gauge needle may provide the fluid dynamics required for high flow rate procedures, the inherent reduction in septum puncture life is not sustainable for frequently repeated procedures such as apheresis and hemodialysis.

Figure 4A:
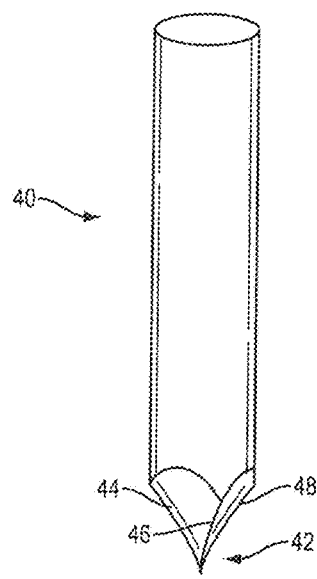
FIG. 4A provides a schematic view of a conventional 16 gauge trocar needle as recognized in the art.
Figure 4B:
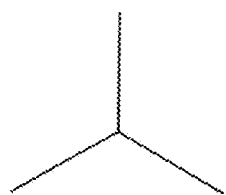
FIG. 4B provides a schematic top-view of a three-legged insertion profile using the trocar of FIG. 4A.
Figure 4C:
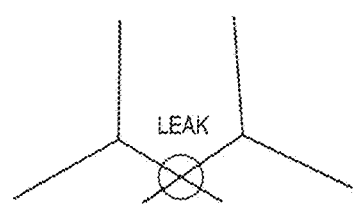
FIG. 4C provides a schematic top view of overlapping three-legged insertion profiles using the trocar of FIG. 4A.
Figure 4D:
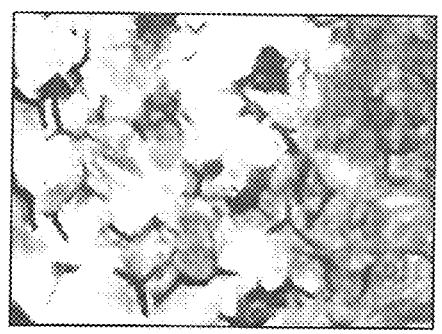
FIG. 4D depicts multiple and overlapping three-legged insertion sites through a septum using the trocar of FIG. 4A.
Figure 4E:
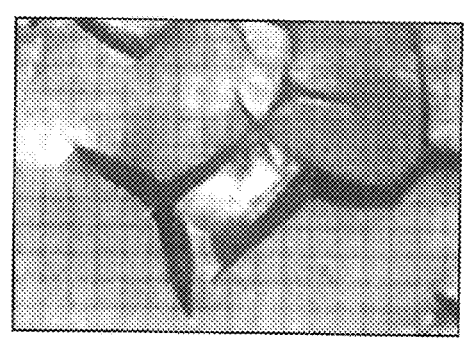
FIG. 4E depicts a magnified view of an overlapping three-legged insertion site of FIG. 4D.
Figure 5A:
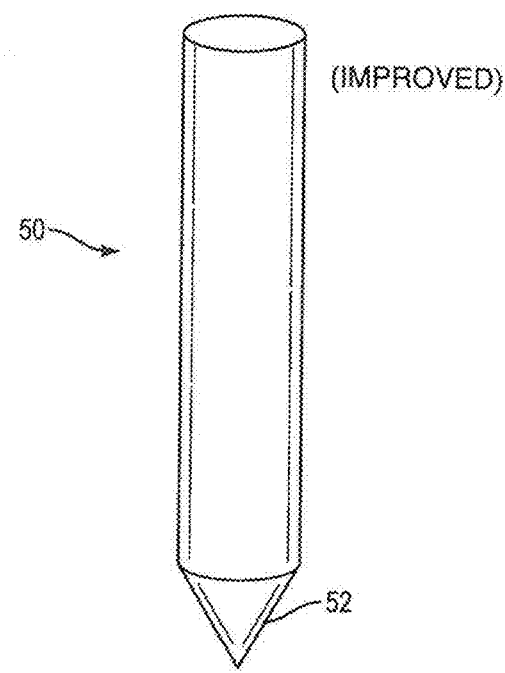
FIG. 5A provides a schematic view of a rounded singular point trocar, in accordance with one embodiment of the present invention.
Figure 5B:
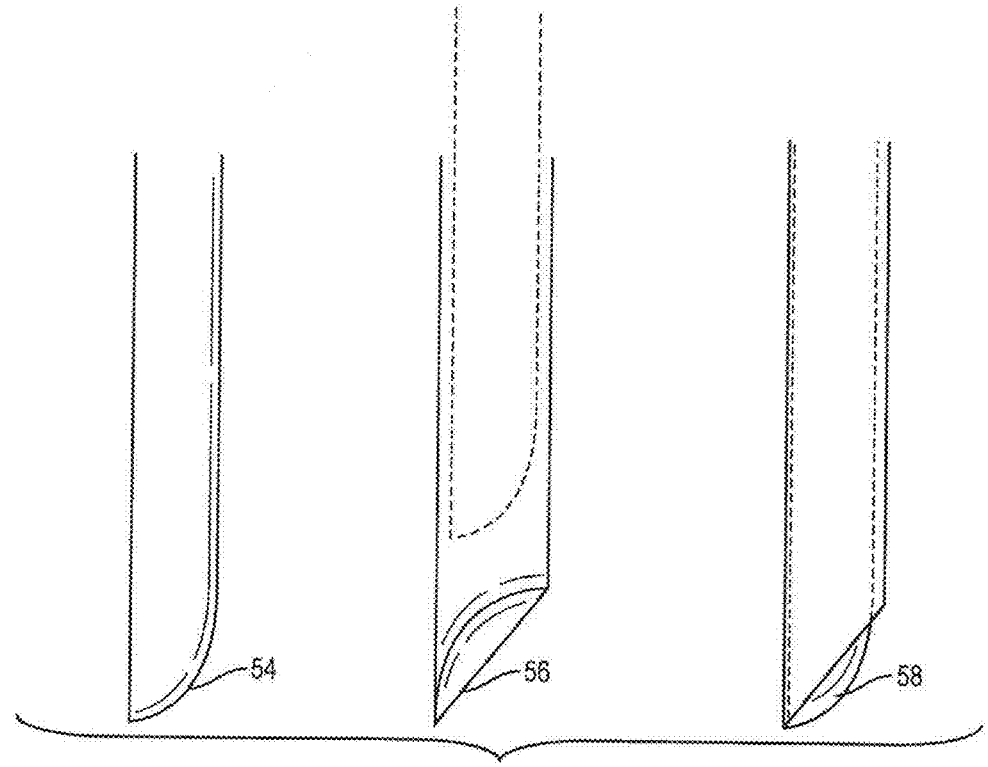
FIG. 5B provides a schematic side view a trocar that includes a unidirectional face, in accordance with one embodiment of the present invention.

FIG. 4A depicts a standard 16 gauge trocar needle 40 that includes a pointed tip 42 with three sharp edges 44, 46, 48 that create three-legged insertion profile (FIG. 4B) when advanced through the surface of an elastomeric septum. As shown in FIG. 4C, a gap is created when the legs of one or more adjacent puncture sites overlap, increasing the likelihood of the septum leaking from that location. As shown in FIG. 4D and FIG. 4E (magnified), repeated punctures of an elastomeric septum with the trocar such as the one depicted in FIG. 4A create multiple overlapping puncture sites that eventually compromise the integrity of the septum. Referring to FIG. 5A, in one embodiment an improved trocar needle 50 replaces the sharp edges of the conventional trocar tip with a singular rounded point 52. Replacing the sharp/rigid cutting edges with a smooth pointed surface increases the puncture life of the septum by providing a reduced insertion profile that decreases the likelihood of adjacent puncture sites overlapping. Referring to FIG. 5B, in another embodiment an improved trocar design includes a unidirectional face 54 configured to mirror the bevel of the needle opening 56. When inserted into the shaft of the needle, the unidirectional face 54 at the tip of the trocar conforms to the bevel of the needle opening 56 to create a solid unitary pointed tip 58. Unlike the rounded trocar of FIG. 5A, in which the septum is punctured entirely by the trocar tip, the pointed tip depicted in FIG. 5B represents the combined points of the needle opening and trocar.

Figure 6A:
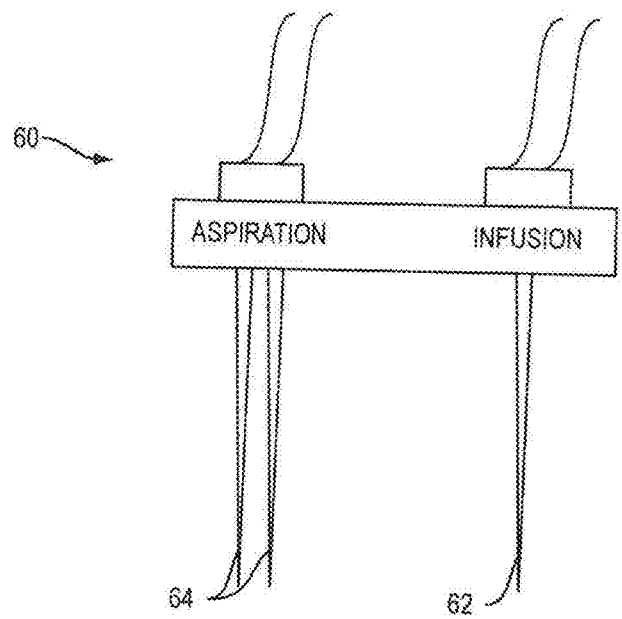
FIG. 6A provides a schematic side view a needle aspiration and infusion system, in accordance with one embodiment of the present invention.

Referring to FIG. 6A, in one embodiment an infusion needle assembly 60 comprising two non-coring 19 gauge needles 64 for penetrating the septum of the aspiration reservoir 22 (not shown) and a single 19 or 20 gauge needle 62 for penetrating the septum of the infusion reservoir 24 (not shown). In one embodiment, the two non-coring 19 gauge needles are connected to each other by tubing that bifurcates to form a y-site such that a medical professional can simultaneously puncture the septum of the aspiration reservoir with both needles. The embodiment depicted in FIG. 6A is not intended to limit the arrangement, orientation, gauge or number of needles used to penetrate the septum of the aspiration or infusion reservoirs. Table 1 provides a comparison of the inner diameter (ID) of various needle sizes, along with the corresponding number of needles of each gauge required to meet the internal cross-sectional area of a 16 gauge needle. Any number and/or combination of needles in Table 1 can be used to access the aspiration and/or infusion lumens described herein, depending on the desired flow rate, clinical application and condition of the patient.

TABLE 1

| Needle Size | ID (in) | Area (in^2) | # of needles to equal 16 G Area |
|---|---|---|---|
| 16 G | 0.047 | 0.00694 | 1 |
| 17 G | 0.042 | 0.00554 | 1.25 |
| 18 G | 0.033 | 0.00342 | 2.03 |
| 19 G | 0.027 | 0.00229 | 3.03 |
| 20 G | 0.02375 | 0.00177 | 3.92 |
| 22 G | 0.01625 | 0.00083 | 8.37 |

Although two non-coring 19 gauge needles provide less cross-sectional area than a single 16 gauge needle, the fluid pressure they achieve is sufficiently similar to that of 16 gauge needle to prevent the aspiration lumen from constricting and/or collapsing upon itself. The ability of two 19 gauge needles to achieve fluid pressures that maintain aspiration lumen integrity similar to one 16 gauge needle while providing a higher clinically acceptable number of septum punctures represents a significant clinical advantage for high flow procedures.

Figure 6B:
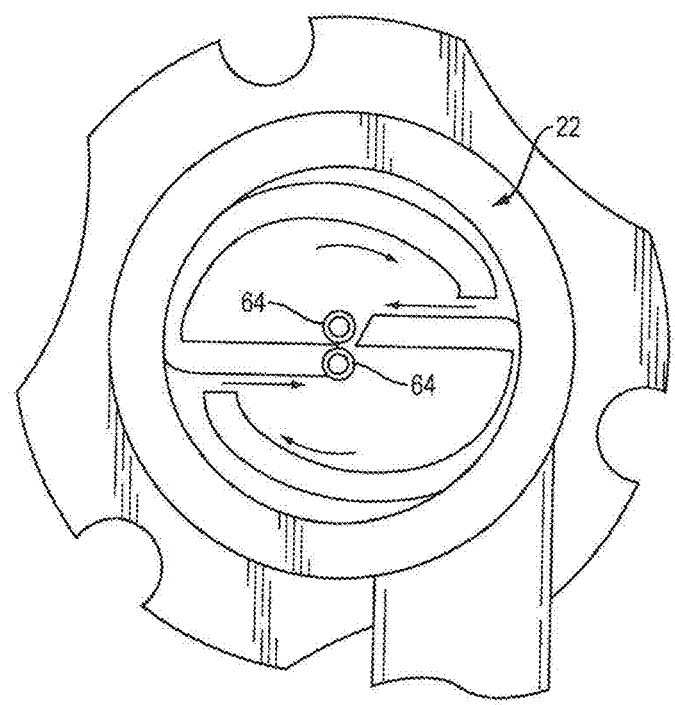
FIG. 6B provides a top view of an aspiration reservoir with vortex fluid flow, in accordance with one embodiment of the present invention.

In one embodiment, fluid flow may be further optimized by adjusting the orientation of each needle opening (i.e., bevel) in the needle assembly depicted in FIG. 6A. Since the position of the multi-reservoir port is visible underneath the skin, the openings of the linked non-coring needles may be positioned such that they face directly towards the inlet lumen. Alternatively, as shown in FIG. 6B, in another embodiment the openings of the linked non-coring needles 64 (top view) are positioned such that they face in substantially opposite directions to facilitate vortex (i.e., spiral) flow within the aspiration reservoir. As described in U.S. Pat. No. 5,951,512 assigned to Angiodynamics, Inc. of Latham, N.Y., incorporated herein by reference, vortex flow within a port reservoir provides a number of benefits, including the prevention of unwanted buildup of blood components within the port reservoirs. As indicated by the direction of the arrows, facing the aspiration needles 64 such that their respective openings face opposite directions encourages the fluid to flow in a vortex pattern within the aspiration reservoir. The pattern of flow depicted in FIG. 6B allows fluid to flow into each needle opening from opposite, and therefore non-competing, portions of the circulating vortex. It should be appreciated that vortex flow can be established in both the aspiration reservoir (i.e., as fluid is drawn into the needle openings) and infusion reservoir (i.e., as fluid flows out of the needle openings) by adjusting the orientation of the needle opening(s) within the aspiration or infusion reservoir.

Figure 7A:
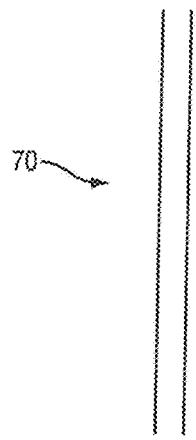
FIGS. 7A-C provide schematic side views of needle shaft designs, in accordance with embodiments of the present invention.
Figure 7B:
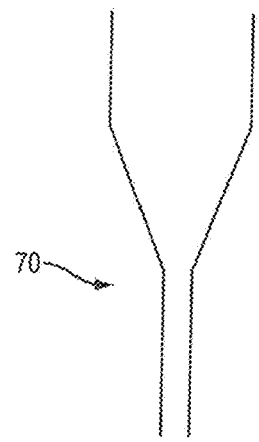
Figure 7C:
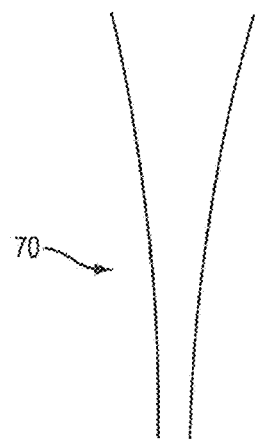

In yet another embodiment, flow rates through the aspiration and/or infusion needle assemblies can be further optimized by using needle shaft designs that reduce the pressure required to meet the desired flow rates. For example, the length of the small inner diameter of a needle of standard length and shape (FIG. 7A) can be minimized by providing a needle shaft that flares (FIG. 7B) or gradually tapers (FIG. 7C) to a wider inner diameter at a point above the needle tip, thereby reducing the pressure drop over the length of the needle. The wider portions of the needle shaft of FIGS. 7B and 7C are sufficiently distant from the pointed tip of the needle to cause minimal trauma to both the patient and port septum.

Since ports are fully implanted within the body, their service life is limited in large part by the durability (i.e., puncture life) of the septum. Septum puncture life, and therefore the life of the multi-reservoir port, can be optimized by careful selection of the septum material and the dimensions of the septum within the port assembly. Examples of needle-penetrable and self-sealable materials include, but are not limited to, silicone and related elastomeric materials. Regardless of the material used, after a threshold number of needle punctures the septum becomes damaged and is no longer able to re-seal itself. Once the integrity of the septum is compromised to the point that it can no longer prevent fluid leakage, either into or out of the port reservoir, it is necessary to replace the entire port assembly, and possibly the attached catheter as well. Generally, the ability of a septum to self-seal and resist coring is directly related to the durometer of the material it is constructed from. While low durometer materials tends to reduce coring, they are not as effective at self-sealing after withdrawal of the needle. Similarly, high durometer materials promote better self-sealing after needle withdrawal, but tend to core relatively easily. Due to these competing requirements, the septum of conventional implantable ports generally include elastomeric materials having a durometer that resists coring and is capable of self-sealing, but is not optimal for either criteria.

Figure 8A:
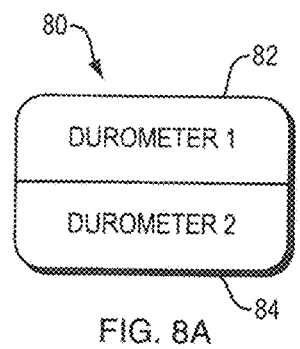
FIGS. 8A-C provide a schematic illustrations of various multi-durometer septum designs, in accordance with one embodiment of the present invention.
Figure 8B:
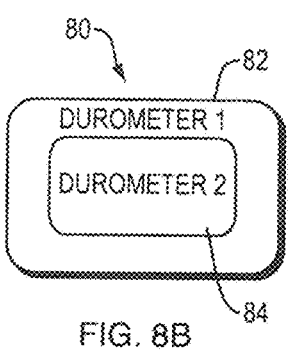
Figure 8C:
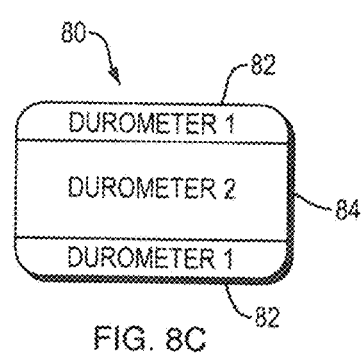

In another embodiment, the present invention provides a septum comprising a dual-durometer elastomeric material that includes one layer configured to minimize coring (i.e., a low durometer material) and a second layer configured for optimal self-sealing (i.e., a high durometer material). Optimizing the self-sealing and non-coring capabilities of the septum with a dual-durometer materials enhances flow rates throughout the system by allowing repeated penetration with large gauge needles. For example, as shown in FIG. 8A, a dual-durometer septum 80 can be formed during the molding process to preferably include a top layer 82 (i.e., the layer closest to the patient's skin) comprising a low durometer material to reduce coring, and a bottom layer 84 (i.e., the layer closest to the port reservoir) comprising a high durometer material to promote self-sealing. While the top and bottom layers of FIG. 8A are depicted as being of substantially the same thickness, it should be understood that the thickness and orientation of either layer may be adjusted according to the clinical application and needs of the patient. For example, as shown in FIG. 8B, a thin layer of a low durometer material 82 may enclose (i.e., surround, encapsulate, encase etc.) a proportionally thicker layer of a high durometer material 84. Alternatively, as shown in FIG. 8C, the layer of high durometer material 84 may be disposed between top and bottom layers of low durometer material 82.

Figure 9A:
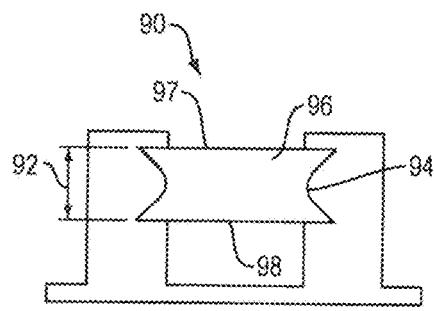
FIGS. 9A-C provide a schematic side view of septum and port geometries, in accordance with embodiments of the present invention.
Figure 9B:
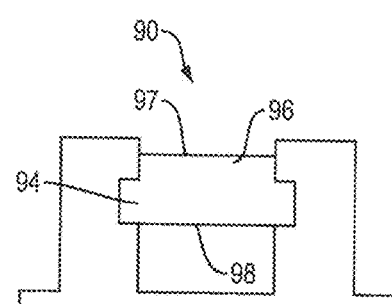
Figure 9C:
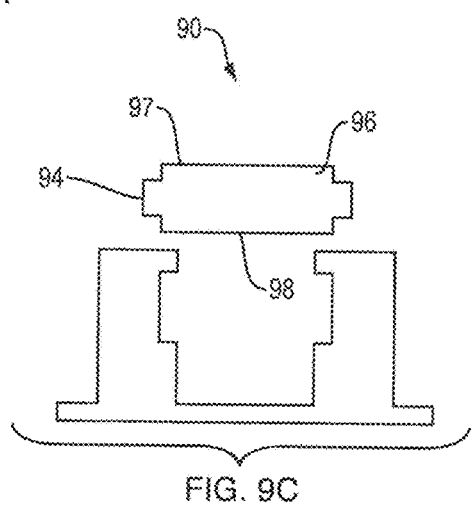

In another embodiment, the dual-durometer characteristics of the multi-layer septum of FIGS. 9A-C may be achieved by applying varying degrees of radially inward compressive force along the height 92 of a single-layer septum to create high and low durometer regions throughout the length of the septum. Inward compression increases the ability of the septum to re-seal puncture sites by pushing the edges of puncture holes together. Portions of the septum that receive little, or no, inward compression provide improved self-sealing due to their decreased susceptibility to coring. In one embodiment, the radially compressive inward force is created by placing a septum having a constant cylindrical shape within a port housing that includes a varying inner diameter. For example, the port housing of FIG. 9A includes an inner wall 94 configured to exert a radially compressive inward force to the middle portion of the septum 96, and incrementally less compression along the top 97 and bottom 98 portions of the septum. Similar to the dual-durometer septum of FIG. 8C, the septum configuration of FIG. 9A provides a high durometer middle layer 96 disposed between low durometer top 97 and bottom 98 layers. The durometer gradient created by the port housing of FIG. 9A ensures that the self-sealing inner portion of the septum is surrounded by top and bottom layers that are increasingly resistant to coring (i.e., top and bottom surfaces). FIG. 9B illustrates another embodiment, in which a radially compressive inward force is applied primarily to the top 97 of the septum to provide a high durometer top layer and a low durometer bottom layer 98. In another embodiment, the radially compressive inward force results from placing a septum with a varying outer diameter (OD) within a port housing. For example, the septum of FIG. 9C includes a middle portion 96 that is wider than the top 97 and bottom 98 portions such that the port housing primarily compresses the middle portion 96 of the septum. Similar to the dual-durometer septum of FIG. 8C, the septum of FIG. 9C provides a high durometer middle layer 96 disposed between low durometer top 97 and bottom layers 98. The septum geometries and port housing geometries described herein are provided by way of non-limiting example. It should be appreciated that the present invention contemplates a variety of septum and port geometries beyond those disclosed herein.

Figure 10A:
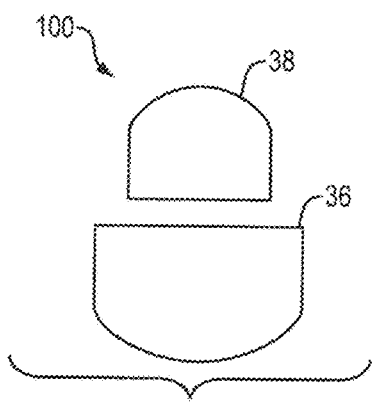
FIGS. 10A-D provide schematic illustration of various dual-lumen catheter designs, in accordance with one embodiment of the present invention.
Figure 10B:
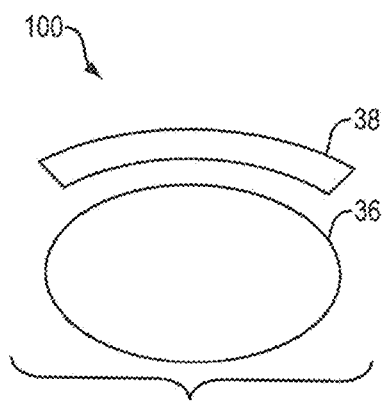
Figure 10C:
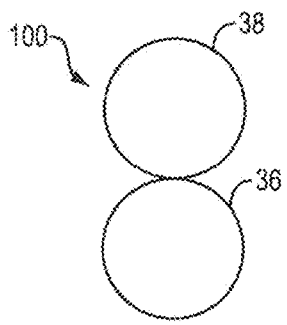
Figure 10D:
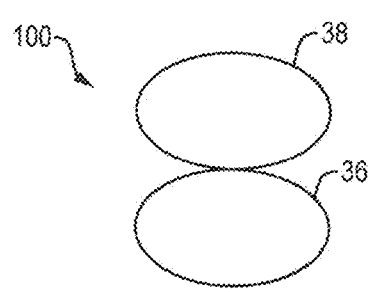
Figure 11:
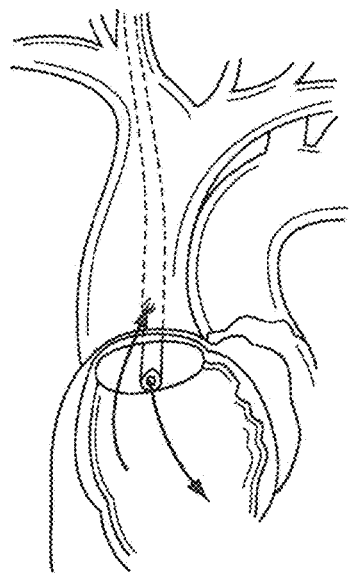
FIG. 11 depicts the placement of a staggered-tip dual-lumen catheter within a patient, in accordance with one embodiment of the present invention.

In one embodiment, flow rates may be further optimized by providing a dual-lumen catheter that includes an aspiration lumen that is over-sized as compared to the infusion lumen. The larger diameter of the aspiration lumen ensures that fluid flows from the proximal end of the catheter to the aspiration reservoir under minimal pressure. An additional benefit of using a dual-lumen that includes differently shaped aspiration and infusion lumens is that it becomes practically impossible to connect the distal end of the catheter to the incorrect inlet or outlet stem. As illustrated in FIG. 10A, the aspiration 36 and infusion 38 lumens may both include D-shapes, with the aspiration lumen having a larger internal diameter than the infusion lumen. Alternatively, as illustrated in FIG. 10B, the dual-lumen catheter may include a substantially oblong aspiration lumen 36 and a concave infusion lumen 38. An over-sized aspiration lumen is particularly useful for hemodialysis procedures, which require flow rates of at least 400 ml/min. However, the over-sized aspiration lumens required for hemodialysis may be unnecessarily larger for the comparatively low 150 ml/min flow rates required for apheresis. Referring to FIGS. 10C and 10D, dual-lumen catheters may be designed specifically for apheresis that include aspiration 36 and infusion 38 lumens that are both substantially circular (i.e., round, oval, oblong, elliptical etc.). Circular shaped lumens remain capable of proving the flow rates required for apheresis and provide better structural support than D-shaped designs to prevent the aspiration lumen from collapsing under negative pressure. As discussed above, the integrity of the infusion lumen is not an issue because fluid flows though the infusion lumen under positive pressure. However, a dual-lumen catheter in which both lumens are substantially circular is still beneficial because medical professionals commonly reverse the aspiration and infusion lumens during treatment. For example, if the aspiration lumen has a fibrin sheath buildup or other blockage reversing the direction of flow such allows blockages to be flushed away (i.e., into circulation). Thus, it remains important to have an infusion lumen capable of withstanding the negative pressures associated with an aspiration lumen.

All of the systems, assemblies and/or methods disclosed and claimed herein can be made and executed without undue experimentation in light of the present disclosure. While the present invention have been described in terms of preferred embodiments, it will be apparent to those of skill in the art that variations can be applied to the systems, assemblies and/or methods described herein without departing from the concept, spirit and scope of the invention. All such similar substitutes and modifications apparent to those skilled in the art are deemed to be within the spirit, scope and concept of the invention as defined by the appended claims.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A multi-reservoir port system, comprising:
    a vascular access port, including:
        a housing defining first and second reservoirs,
        a first septum mounted within the housing sealing the first reservoir, the first septum comprising an elastomeric material having a first septum first layer having a first durometer and a first septum second layer having a second durometer, the first septum second layer being encapsulated on all sides by the first septum first layer,
        a second septum mounted within the housing sealing the second reservoir, the second septum comprising an elastomeric material having a second septum first layer having a first durometer and a second septum second layer having a second durometer, the second septum second layer being encapsulated on all sides by the second septum first layer,
        an inlet stem having an inlet lumen in fluid communication with the first reservoir, and
        an outlet stem having an outlet lumen in fluid communication with the second reservoir; and
    a dual-lumen catheter having a proximal end, a distal end, and first and second lumens extending therebetween;
    wherein the inlet stem is dimensioned to receive the first lumen at the proximal end of the catheter; and
    wherein the outlet stem is dimensioned to receive the second lumen at the proximal end of the catheter.

2. The assembly of claim 1, wherein the durometer of the first septum first layer and second septum first layer are less than the durometer of the first septum second layer and the second septum second layer.

3. The assembly of claim 1, wherein the thickness of the first septum second layer and second septum second layer is greater than the thickness of the first septum first layer and second septum first layer.

4. A multi-reservoir port and needle system, comprising:
    a vascular access port, including:
        a housing defining first and second reservoirs,
        a first septum mounted within the housing sealing the first reservoir, the first septum comprising an elastomeric material having a first septum first layer having a first durometer and a first septum second layer having a second durometer, the first septum second layer being encapsulated on all sides by the first septum first layer,
        a second septum mounted within the housing sealing the second reservoir, the second septum comprising an elastomeric material having a second septum first layer having a first durometer and a second septum second layer having a second durometer, the second septum second layer being encapsulated on all sides by the second septum first layer,
        an inlet stem having an inlet lumen in fluid communication with the first reservoir, and
        an outlet stem having an outlet lumen in fluid communication with the second reservoir; and
    a needle assembly, including:
        at least one infusion needle; and
        at least two aspiration needles wherein the at least two aspiration needles are attached to each other so as to be parallel of one another;
    wherein the infusion needle is configured to penetrate the second septum of the vascular access port, and the at least two aspiration needles are configured to penetrate the first septum of the vascular access port.

5. The assembly of claim 4, wherein the at least one infusion needle and at least two aspiration needles are non-coring.

6. The assembly of claim 4, wherein the at least one infusion needle and at least two aspiration needles are at least 19 gauge.

7. The assembly of claim 4, wherein each of the at least two aspiration needles include openings that face in opposite directions.

8. The assembly of claim 4, wherein the at least two aspiration needles are attached to each other.

9. The assembly of claim 4, wherein the at least two aspiration needles are in fluid communication with the aspiration reservoir.

10. The assembly of claim 4, wherein the infusion needle is in fluid communication with the infusion reservoir.

11. The assembly of claim 4, wherein the at least one infusion needle and at least two aspiration needles are in fluid communication with a blood circulation apparatus.

12. The assembly of claim 11, wherein the blood circulation apparatus includes a dialysis machine or an apheresis machine.

13. A method of performing apheresis, comprising:
   implanting a multi-reservoir vascular access port, the multi-reservoir vascular access port comprising:
      a housing defining an aspiration reservoir and an infusion reservoirs,
      a first septum mounted within the housing sealing the aspiration reservoir, the first septum comprises an elastomeric material having a first septum first layer having a first durometer and a first septum second layer having a second durometer, the first septum second layer being encapsulated on all sides by the first septum first layer,
      a second septum mounted within the housing sealing the infusion reservoir, the second septum comprises an elastomeric material having a second septum first layer having a first durometer and a second septum second layer having a second durometer, the second septum second layer being encapsulated on all sides by the second septum first layer;
   accessing the aspiration reservoir of the multi-reservoir vascular access port with an aspiration needle assembly;
   accessing the infusion reservoir of the multi-reservoir vascular access port with an infusion needle assembly;
   flowing fluid from the aspiration reservoir through the aspiration needle assembly to an apheresis machine; and
   flowing fluid from the apheresis machine to the infusion reservoir through the infusion needle assembly.

14. The method of claim 13, wherein the needles of the aspiration needle assembly and infusion needle assembly are non-coring 19 gauge needles.

\* \* \* \* \*